United States Patent [19]

Lafon

[11] 4,209,523

[45] Jun. 24, 1980

[54] ACETOHYDROXAMIC ACIDS

[75] Inventor: Louis Lafon, Paris, France

[73] Assignee: Laboratoire L. Lafon, Maisons Alfort, France

[21] Appl. No.: 930,924

[22] Filed: Aug. 4, 1978

Related U.S. Application Data

[62] Division of Ser. No. 778,543, Mar. 17, 1977, Pat. No. 4,122,186.

[30] Foreign Application Priority Data

Mar. 23, 1976 [GB] United Kingdom ............... 11710/76
Feb. 15, 1977 [GB] United Kingdom ............... 06298/77

[51] Int. Cl.$^2$ .................. A61K 31/415; C07D 235/16
[52] U.S. Cl. .................. 424/273 B; 424/245; 548/326; 548/330; 548/312; 544/32; 544/396; 544/402; 260/239 D; 260/340.5 R; 260/500.5 H; 260/558 R; 260/561 R
[58] Field of Search ............ 424/245, 273 B; 548/326, 330; 260/299

[56] References Cited

U.S. PATENT DOCUMENTS

| | | | |
|---|---|---|---|
| 3,586,694 | 6/1971 | Shen et al. | 548/330 |
| 3,623,882 | 11/1971 | Götze et al. | 548/326 |
| 4,064,136 | 12/1977 | Loew et al. | 548/326 |

*Primary Examiner*—Donald G. Daus
*Assistant Examiner*—James H. Turnipseed
*Attorney, Agent, or Firm*—Poms, Smith, Lande & Rose

[57] ABSTRACT

The invention provides new acetohydroxamic acid derivatives, having interesting properties on the central nervous system, of the formula: $R_1R_2R_3C-CO-NHOH$, in which $R_2$ and $R_3$ are each hydrogen or $C_{1-6}$ alkyl, and $R_1$ is $C_{1-6}$ alkyl $Z_1Z_2N$ (where $Z_1$ and $Z_2$ are each phenyl, substituted phenyl, or cycloalkyl), substituted hydantoinyl, benzhydroxylcarboxamido, $Z_3CH_2-$ (where $Z_3$=optionally substituted aryl), $Z_4-A-$ (where $Z_4$ is optionally substituted phenyl or naphthyl, and A is $-NH-$, $-N(C_{1-4}$ alkyl$)-$, $-N(C_{5-6}$ cycloalkyl$)-$, $-NHCO-$, $-N(C_{1-4}$ alkyl$)CO-$, $-N(C_{5-6}$ cycloalkyl$)CO-$, $-CONH-$, $-CON(C_{1-4}$ alkyl$)-$, $-CON(C_{5-6}$ cycloalkyl$)-$, $-NHCONH-$, $-N(C_5H_6)CONH-$, or $-N($substituted phenyl$)$-CONH$-$, optionally substituted benzimidazolyl, or an optionally substituted tricyclic radical, and their metal and acid addition salts.

4 Claims, No Drawings

ACETOHYDROXAMIC ACIDS

This is a division of application Ser. No. 778,543 filed Mar. 17, 1977 now issued on Oct. 24, 1978 as U.S. Pat. No. 4,122,186.

The present invention provides the acetohydroxamic acids of the formula I below, and their metal salts. It also provides a process for the preparation of these compounds and compositions containing them.

Various hydroxamic acids have already been described, some of which, especially 4-α-naphthyloxy-3-hydroxybutyrohydroxamic acid [cf. Example 5 (Comparative example) of U.S. Pat. No. 3,819,702] have proved inactive in therapy, while others, especially 4-phenylsulphinylbutyrohydroxamic acid, 4-(p-fluorophenylsulphinyl)-butyrohydroxamic acid, 3-(p-fluorophenylsulphinyl)-propionohydroxamic acid and 4-(p-chlorophenylsulphinyl)-butyrohydroxamic acid and β-benzhydrylsulphinyl-acetohydroxamic acid, 3-benzhydrylsulphinyl-propionohydroxamic acid and 4-benzhydrylsulphinyl-butyrohydroxamic acid have proved of interest in the treatment of the central nervous system.

The new acetohydroxamic acids are useful in therapy in treating the central nervous system (CNS), especially as psychotropic agents.

The new products of the invention have the general formula

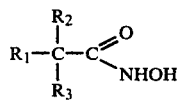

in which $R_2$ and $R_3$, which may be identical or different, each represent a hydrogen atom or a $C_1$-$C_6$-alkyl group and $R_1$ represents a $C_1$-$CH_6$-alkyl group, a N,N-disubstituted carbamoyl group of the formula

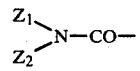

(where $Z_1$ and $Z_2$, which may be identical or different, each represent a $C_5$-$C_6$-cycloalkyl group, a phenyl group or a phenyl group substituted especially by one or more $C_1$-$C_4$-alkyl groups, $C_1$-$C_4$-alkoxy groups, methylenedioxy groups, halogen, $NH_2$, $NO_2$ or $CF_3$ groups), a 3-hydantoinyl group of the formula

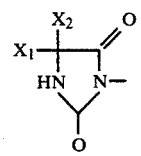

(where $X_1$ is a phenyl group which is optionally substituted, especially by one or more $C_1$-$C_4$-alkyl groups, $C_1$-$C_4$-alkoxy groups, $NH_2$, halogen or $CF_3$ groups, and $X_2$ is H, a $C_1$-$C_6$-alkyl group or a phenyl group optionally substituted by one or more $C_1$-$C_4$-alkyl groups, $C_1$-$C_4$-alkoxy groups, methylenedioxy groups, halogen, $CF_3$, $NO_2$ or $NH_2$ groups), a benzhydrylcarboxamido group of the formula

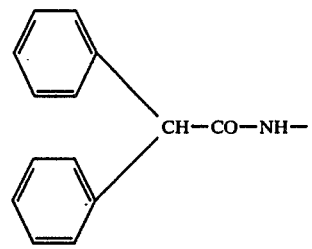

(where each of the phenyl groups can in particular be substituted by one or more $C_1$-$C_4$-alkyl groups, $C_1$-$C_4$-alkoxy groups, halogen, $NH_2$, $CF_3$ or $NO_2$ groups), an arylsulphinyl group of the formula

(where $Z_3$ is an aryl group, especially an α-naphthyl, β-naphthyl or phenyl group, each of which can be substituted, especially by one or more $C_1$-$C_4$-alkyl groups, $C_1$-$C_4$-alkoxy groups, halogen, $NH_2$, $CF_3$, $NO_2$ or methylenedioxy groups), a

group where $Z_4$ is a phenyl group, an α-naphthyl group, a β-naphthyl group (each phenyl nucleus of these groups being optionally substituted, especially by one or more $C_1$-$C_4$-alkyl groups, $C_1$-$C_4$-alkoxy groups, methylenedioxy groups, halogen, $CF_3$, $NH_2$ or $NO_2$ groups) or an adamantyl group, and A represents —NH—, —N($C_1$-$C_4$-alkyl)-, —N($C_5$-$C_6$-cycloalkyl)-, —NHCO—, —N($C_1$-$C_4$-alkyl)CO—, —N($C_5$-$C_6$-cycloalkyl)CO—, CONH—, —CON($C_1$-$C_4$-alkyl)-, —CON($C_5$-$C_6$-cycloalkyl)—, —NHCONH—, N($C_6H_5$)CONH—, N(substituted phenyl)CONH— or

where $Z_4$ can represent an optionally substituted benzhydryl group if A is different from —CONH—], a benzimidazolyl group of the formula:

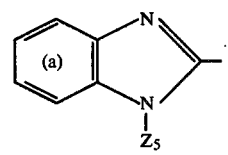

(where $Z_5$ is an aryl group, especially a phenyl group, the said aryl group and the nucleus (a) being optionally substituted by one or more $C_1$-$C_4$-alkyl groups, $C_1$-$C_4$-alkoxy groups, methylenedioxy groups, halogen, $CF_3$, $NO_2$ or $NH_2$ groups) or a tricyclic group (T) of the formula

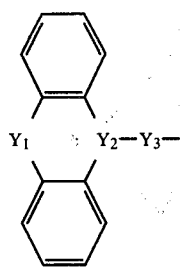

where $Y_1$ is a simple bond, $-CH_2-$, $-CH=CH-$, $-CH_2CH_2-$, $-S-$, $-O-$, $-SCH_2-$ or $-OCH_2-$, $Y_2$ is

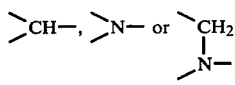

and $Y_3$ is a simple bond or a $-CH_2-$ or $-CO-$ group, and where each of the phenyl nuclei can be substituted, especially by one or more $C_1$-$C_4$-alkyl groups, $C_1$-$C_4$-alkoxy groups, methylenedioxy groups, halogen, $CF_3$, $NO_2$ or $NH_2$ groups); and their metal salts, and their addition salts with acids, if $R_1$ contains a basic radical.

Amongst the metal salts which can be used there may in particular be mentioned the alkali metal salts, the alkaline earth metal salts, the zinc salts, the magnesium salts and the aluminium salts, for example the salts which correspond to the formula

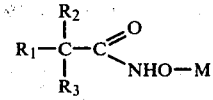

Ia where M is Na, K, ½Ca, ½Zn, ½Mg or ⅓Al.

By halogen atom there is here understood an atom of fluorine, chlorine, bromine or iodine. The preferred halogen atoms are the atoms of fluorine, chlorine and bromine, from the pharmacological point of view, and the atoms of chlorine and bromine from the point of view of the synthesis reaction mechanisms.

If the group A represents the -N(substituted phenyl) CONH- group, the phenyl nucleus can be substituted by one or more $C_1$-$C_4$-alkyl groups, $C_1$-$C_4$-alkoxy groups, methylenedioxy groups, halogen, $CF_3$, $NO_2$ or $NH_2$ groups. In the same way, if $Z_4$ represents a benzhydryl group, each of the two phenyl nuclei of the said benzhydryl group can be substituted by one or more $C_1$-$C_4$-alkyl groups, $C_1$-$C_4$-alkoxy groups, methylenedioxy groups, halogen, $CF_3$, $NO_2$ or $NH_2$ groups.

A certain number of compounds according to the invention have been listed in Table I below, without implying any limitation.

TABLE I $$R_1-\underset{\underset{R_3}{|}}{\overset{\overset{R_2}{|}}{C}}-C\overset{O}{\underset{NHO-X}{\diagdown}}$$

| Example | Code Number | $R_1$ | $R_2$ | $R_3$ | X | Melting point |
|---|---|---|---|---|---|---|
| 1 | CRL 40373 | $CH_3CH_2CH_2CH_2-$ | $CH_3(CH_2)_3-$ | $CH_3(CH_2)_3-$ | H | 133°-134° C. |
| 2 | CRL 40382 | ![](C6H5 / C6H5 / H-N N- / =O structure) | H | H | H | (a) |
| 3 | CRL 40385 | $(C_6H_5)_2N-CO$ | H | H | H | 150°-151° C. |
| 4 | CRL 40400 | $(C_6H_5)_2CHCONH-$ | H | H | H | 156° C. |
| 5 | CRL 40411 | Cl-C6H4-CH2-SO- | H | H | H | 210° C. (b) |
| 6 | CRL 40258 | phenothiazinyl-N-CH2- | H | H | Na | 155°-160° C. (b) |
| 7 | CRL 40438 | $(C_6H_5)_2N-CO-$ | $CH_3$ | H | H | 171°-172° C. |
| 8 | CRL 40439 | $(C_6H_5)_2N-CO-$ | $CH_3CH_2$ | H | H | 159°-160° C. |
| 9 | CRL 40446 | N,N-dicyclohexyl-carbamoyl | H | H | H | 198°-200° C. (b) |
| 10 | CRL 40447 | C6H5 / C6H5 / HN N- / =O structure | $CH_3$ | H | H | (c) |

TABLE I-continued $$\begin{array}{c} R_2 \\ | \\ R_1-C-C \\ | \\ R_3 \end{array} \begin{array}{c} O \\ \| \\ NHO-X \end{array}$$

| Example | Code Number | R₁ | R₂ | R₃ | X | Melting point |
|---|---|---|---|---|---|---|
| 11 | CRL 40450 | C₆H₅–C(CH₂CH₃)(NH–CO–N<)– (hydantoin-type ring, C=O) | H | H | H | 201°–202° C. |
| 12 | CRL 40464 | 4-Cl–C₆H₄–NH–CO– | H | H | H | 212°–213° C. (b) |
| 13 | CRL 40465 | 3,4-Cl₂–C₆H₃–CH₂–SO– | H | H | H | 191°–192° C. |
| 14 | CRL 40466 | 4-Cl–C₆H₄–CH₂–SO– | CH₃ | H | H | 132°–133° C. |
| 15 | CRL 40468 | (p-ClC₆H₄)(p-ClC₆H₄)C(NH–CO–N<)– (hydantoin-type ring, C=O) | H | H | H | 139°–141° C. |
| 16 | CRL 40471 | 10,11-dihydro-5H-dibenzo[b,f]azepine-5-carbonyl (N–CO–) | H | H | H | 201°–202° C. (b) |
| 17 | CRL 40472 | 4-NH₂–C₆H₄–NH–CO– | H | H | H | 216°–220° C. (b) (d) |
|  |  | hydrochloride |  |  |  |  |
| 18 | CRL 40473 | 4-NH₂–C₆H₄–CO–NH– | H | H | H | 182°–185° C. (b) |
|  |  | hydrochloride |  |  |  |  |
| 19 | CRL 40475 | naphth-1-yl–CH₂–SO– | H | H | H | 209°–210° C. |
| 20 | CRL 40490 | 1-phenyl-2-methyl-benzimidazol-yl | H | H | H | 212°–215° C. (b) |

TABLE I-continued $$\begin{array}{c} R_2 \\ | \\ R_1-C-C \\ | \\ R_3 \end{array} \begin{array}{c} O \\ \| \\ NHO-X \end{array}$$

| Example | Code Number | R₁ | R₂ | R₃ | X | Melting point |
|---------|-------------|----|----|----|---|---------------|
| 21 | CRL 40491 | 3,4-dichlorophenyl-NH-CO- | H | H | H | 201°–202° C. |
| 22 | CRL 40500 | 3,4-dichlorophenyl-NH- | H | H | H | 138°–140° C. |
| 23 | CRL 40509 | 3,4,5-trimethoxyphenyl-NH-CO- | H | H | H | 195°–196° C. |
| 24 | CRL 40512 | 3-trifluoromethylphenyl-NH-CO- | H | H | H | 206°–207° C. |
| 25 | CRL 40510 | 2,6-dichlorophenyl-NH-CO- | H | H | H | 175°–176° C. |
| 26 | CRL 40513 | phenyl-NH-CO-NH- | H | H | H | 165°–166° C. |
| 27 | CRL 40511 | 4-fluorophenyl-CH₂-SO- | H | H | H | 177° C. |
| 28 | CRL 40498 | 4-methoxyphenyl-CH₂-SO- | H | H | H | 159° C. |
| 29 | CRL 40515 | 2,4-dichlorophenyl-CH₂-SO- | H | H | H | 204°–205° C. |
| 30 | CRL 40516 | 2,6-dichlorophenyl-CH₂-SO- | H | H | H | 201° C. |
| 31 | CRL 40539 | 4-nitrophenyl-CH₂-SO- | H | H | H | 227° C. |

TABLE I-continued $$R_1-\underset{\underset{R_3}{|}}{\overset{\overset{R_2}{|}}{C}}-\underset{NHO-X}{\overset{\nearrow O}{C}}$$

| Example | Code Number | R₁ | R₂ | R₃ | X | Melting point |
|---|---|---|---|---|---|---|
| 32 | CRL 40538 | ![benzodioxole-CH₂-SO-] | H | H | H | 206° C. |
| 33 | CRL 40564 | ![3,4-dimethoxyphenyl-CH₂-SO-] | H | H | H | 202° C. |
| 34 | CRL 40517 | ![4-chlorophenyl-NH-CO-NH-] | H | H | H | 220°-222° C. (b) |
| 35 | CRL 40518 | ![naphthyl-NH-CO-] | H | H | H | 184°-186° C. (b) |
| 36 | CRL 40536 | ![(C₆H₅)₂CH-N-piperazinyl-N-] hydrochloride | H | H | H | 206°-208° C. (b) |
| 37 | CRL 40537 | (C₆H₅)₂NHCONH— | H | H | H | 228°-230° C. (b) |
| 38 | CRL 40499 | adamantyl-NH—CO— | H | H | H | 215°-216° C. (b) |

Notes:
(a) double melting point at 132°-134° C. followed by 214°-216° C.
(b) with decomposition
(c) double melting point at 128°-130° C. followed by 205°-206° C.
(d) the free base melts at 164°-165° C.

The hydroxamic acids and their metal salts can be prepared in accordance with a known method, by application of conventional reaction mechanisms. The method proposed according to the invention consists of reacting a corresponding carboxylic acid halide or a $C_1$-$C_3$ lower alkyl carboxylate with hydroxylamine. This reaction is carried out in solution or in suspension in pyridine or in a $C_1$-$C_3$ lower alkanol such as methanol, ethanol, propanol and isopropanol, the reaction mechanism being shown schematically below:

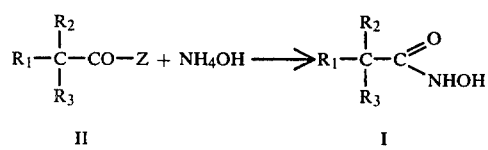

In these formulae, Z is a halogen atom (preferably Cl or Br) or a methoxy, ethoxy, propoxy or isopropoxy group.

If Z is a halogen atom, the acid halide is reacted with hydroxylamine hydrochloride in solution in pyridine. If Z is a $C_1$-$C_3$ lower alkoxy group, the carboxylate is reacted with hydroxylamine hydrochloride in solution or in suspension in a $C_1$-$C_3$-alkanol.

Finally, if $R_1$ contains a sulphinyl group SO, it is possible first to prepare the hydroxamic acid in which $R_1$ contains a mercapto group S and then to oxidise the said mercapto group to the sulphinyl group by means of $H_2O_2$. In that case, it is possible to proceed in accordance with the following reaction mechanism:

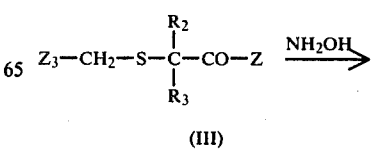

(III)

$$Z_3-CH_2-S-\underset{\underset{R_3}{|}}{\overset{\overset{R_2}{|}}{C}}-C\overset{\nearrow O}{\underset{\searrow NHOH}{}}$$

(IV)

↓ H₂O₂

$$Z_3-CH_2-SO-\underset{\underset{R_3}{|}}{\overset{\overset{R_2}{|}}{C}}-C\overset{\nearrow O}{\underset{\searrow NHOH}{}}$$

(V)

which is illustrated in Example 5 below.

The invention also provides pharmaceutical compositions which comprise at least one compound of the formula I or one of its non-toxic metal salts, in association with a physiologically acceptable excipient.

The invention is illustrated by the examples which follow.

EXAMPLE 1

Tributylacetohydroxamic acid

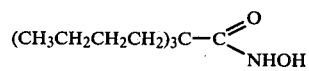

Code No.: CRL 40,373

A solution of 4.56 g (0.02 mol) of tributylacetic acid (melting point: 34°–36° C.; boiling point/0.5 mm Hg=126°–127° C.) in 7.5 ml (0.1 mol) of thionyl chloride is stirred for 30 minutes at 20° C.; the mixture is heated for 1 hour on a waterbath and is evaporated to dryness in vacuo. The acid chloride thus obtained is added dropwise to a solution of 3.5 g (0.05 mol) of hydroxylamine hydrochloride in 25 ml of pyridine. The mixture is stirred for 1 hour at 20° C. and is evaporated to dryness in vacuo, the residue is taken up with 2 N HCl, and the product is filtered off, washed with water, dried, washed with pentane and recrystallised from diisopropyl ether.

CRL 30,373 is obtained in a yield of 48%, melting point: 133°–134° C.

EXAMPLE 2

3-(5,5-Diphenyl-hydantoinyl)-acetohydroxamic acid

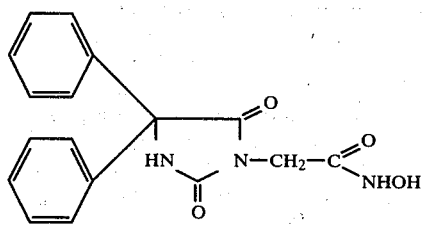

Code No. CRL 40,382

(1) Ethyl 3-(5,5-diphenyl-hydantoin)-acetate

A solution of 12.6 g (0.05 mol) of 5,5-diphenylhydantoin and 6.1 ml (0.055 mol) of ethyl bromoacetate in 100 ml of absolute ethanol is heated under reflux, whilst stirring, and a solution of sodium ethylate prepared from 1.15 g (0.05 gram atom) of sodium and 100 ml of ethanol is run in dropwise over the course of 3 hours. The mixture is heated for a further hour, the sodium bromide is filtered off hot, the filtrate is cooled and the product is filtered off. 16.2 g (96% yield) of ester, melting at 184°–185° C., are obtained.

(2) CRL 40,382

13.6 g (0.04 mol) of ethyl 3-(5,5-diphenyl-hydantoin)acetate are mixed with a solution of hydroxylamine prepared from 4.2 g (0.06 mol) of hydroxylamine hydrochloride and 2.3 g of sodium in 200 ml of methanol. After leaving the reactants in contact overnight at 20° C., the mixture is evaporated to dryness in vacuo, 100 ml of water are added, the mixture is filtered and the filtrate is precipitated with 6 N HCl. The product is filtered off, washed with water, dried and recrystallised from methanol. CRL 40,382 is obtained in a yield of 78%. This product has a double melting point, firstly at 132°–134° C. and secondly at 214°–216° C.

EXAMPLE 3

α-(N,N-Diphenylcarbamoyl)-acetohydroxamic acid

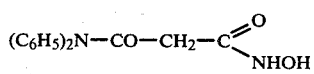

Code No. CRL 40,385

(1) Ethyl N,N-diphenylcarbamoylacetate 7.5 g (0.05 mol) of ethyl-malonyl chloride are run dropwise, whilst stirring, into a solution of 17 g (0.1 mol) of diphenylamine in 150 ml of anhydrous benzene, the reactants are left in contact overnight and the precipitate of diphenylamine hydrochloride is filtered off. The filtrate is washed with 1 N HCl, then with dilute bicarbonate solution and finally with water; it is dried and evaporated to dryness in vacuo, and the residue is taken up in petroleum ether and filtered off. 12 g (85% yield) of ester, melting at 75°–76° C., are obtained.

(2) CRL 40,385

A solution of hydroxylamine is prepared from 7 g (0.1 mol) of hydroxylamine hydrochloride and 3.95 g (0.17 gram atom) of sodium in 250 ml of methanol. The sodium chloride is filtered off, 19.8 g (0.07 mol) of ethyl N,N-diphenylcarbamoylacetate are added and the reactants are left in contact overnight. The mixture is evaporated to dryness in vacuo, the residue is taken up in water, the mixture is filtered, the filtrate is acidified and the precipitate is filtered off, washed with water and with diisopropyl ether, dried and recrystallised from ethanol.

CRL 40,385 is obtained in a yield of 58%. Melting point: 150°–151° C.

EXAMPLE 4

α-(Benzhydrylcarboxamido)-acetohydroxamic acid

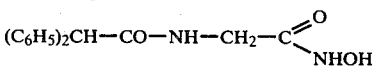

Code No. CRL 40,400

(1) Diphenylacetic acid chloride 21.2 g (0.1 mol) of diphenylacetic acid and 75 ml (about 1 mol) of thionyl chloride are mixed cold. The reaction mixture is heated under reflux for 3 hours and is cooled, the excess thionyl chloride is evaporated and the acid chloride (crystallised at a low temperature, melting point <50° C.) is collected. 22.9 g of acid chloride (yield about 99%) are thus obtained.

(2) Ethyl α-(benzhydrylcarboxamido)-acetate

A solution of 0.2 mol of the ethyl ester of glycine (base) is prepared, in methanol, by neutralising a 10% strength solution, in methanol, of 28 g (0.2 mol) of the corresponding hydrochloride with a solution of sodium methylene (5 g of Na in 50 ml of MeOH, representing about 0.218 mol of methylate). The sodium chloride is filtered off, the methanol is evaporated, the aminoester is diluted with anhydrous benzene, the acid chloride, dissolved in anhydrous benzene, is added at ambient temperature (15°–25° C.) and an exothermic effect is observed during the addition ($T_{max}$ about 35° C.). The whole is then heated under reflux for 2 hours and is cooled, the precipitate formed is filtered off, the benzene is evaporated and an oil is collected, which crystallises in a 50:50 mixture of diethyl ether and diisopropyl ether. The precipitate is filtered off and dried and 19 g of the ethyl ester of α-(benzhydrylcarboxamido)acetic acid are thus collected. Instantaneous melting point: 106°–108° C.; yield: 64%.

(3) CRL 40,400

0.064 mol (19 g) of the preceding ester is dissolved in methanol and a solution, in methanol, of 0.10 mol of hydroxylamine (base) in the presence of an excess of sodium methylate (0.065 mol) is prepared by adding 0.165 mol of sodium methylate to 0.10 mol of hydroxylamine hydrochloride in solution in methanol and filtering off the sodium chloride; the two solutions in methanol are mixed and the reaction mixture is left at ambient temperature for at least 15 hours. The methanol is then evaporated, the residue is taken up in water and acidified by adding 3 N HCl, thus precipitating 16.6 g of CRL 40,400. The precipitate is dried and recrystallised from ethyl acetate. 13 g of CRL 40,400 are thus collected. (Instantaneous melting point: 156° C.; overall yield=46%).

EXAMPLE 5

α-(p-Chlorobenzylsulphinyl)-acetohydroxamic acid

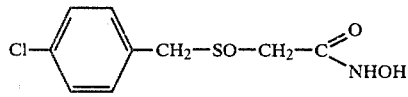

Code No. CRL 40,411

(1) Methyl p-chlorobenzylmercapto-acetate

Anhydrous acetone (100 ml), potassium carbonate (21 g), p-chlorobenzylmercaptan (19.5 ml), methyl chloroacetate (13.2 ml) and potassium iodide (0.1 g) are mixed in the cold. The mixture thus obtained is stirred and heated under reflux for 7 hours. It is cooled, the precipitate ($K_2CO_3$) is filtered off, the acetone is evaporated from the filtrate and the residue is taken up with ether. The ether solution is washed with 4 N NaOH and then with water until the wash waters have a neutral pH. The ether solution is then dried over $MgSO_4$, the ether is evaporated and 34.5 g (100% yield) of methyl p-chlorobenzylmercapto-acetate are collected in the form of a chromatographically pure oil.

(2) p-Chlorobenzylmercapto-acetohydroxamic acid

A solution of 0.15 mol of methyl p-chlorobenzylmercapto-acetate in 50 ml of methanol is mixed with a solution of 0.225 mol of hydroxylamine (base) and 0.15 mol of $CH_3ONa$ in 150 ml of methanol.

The resulting mixture is kept overnight at ambient temperature (15°–25° C.), the methanol is evaporated, the residue is taken up in water and the mixture is acidified with 3 N HCl in order to precipitate the p-chlorobenzylmercaptoacetohydroxamic acid. 31.7 g of the said acid are collected. Yield 91%; melting point: about 130° C.

(3) CRL 40,411

31.7 g (0.091 mol) of p-chlorobenzylmercaptoacetohydroxamic acid are mixed with 100 ml of anhydrous acetic acid and 9.1 ml of hydrogen peroxide of 110 volumes strength are added. The temperature, which is 20° C. at the start, rises and solution of the precipitate formed is also observed. The temperature is maintained at 50° C. and after several minutes it is found that the sulphinyl derivative sets solid. 50 ml of acetic acid are now added and the temperature is kept at 50° C. for 1 hour whilst stirring vigorously. The mixture is cooled and the p-chlorobenzylsulphinyl-acetohydroxamic acid is filtered off. This acid is recrystallised from acetic acid and filtered off, the precipitate is washed with water and with ethanol, and dried, and 31.9 g of CRL 40,411 are collected. Yield 85%; instantaneous melting point 210° C. (with decomposition).

EXAMPLE 6

Sodium β-(10-phenothiazinyl)-propionohydroxamate

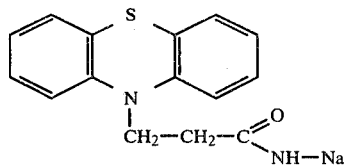

Code No. CRL 40,258

(1) Methyl β-(10-phenothiazinyl)-propionate 25 g of β-(10-phenothiazinyl)-propionitrile dissolved in 200 ml of methanol are heated for 20 hours under reflux with 25 g of sodium hydroxide pellets dissolved in 75 ml of water. The alcohol is evaporated in vacuo, the mixture is filtered over charcoal and is precipitated with concentrated HCl, and the product is filtered off, recrystallised from methanol and dried. 20 g of acid are obtained. Melting point: 161°–162° C. This acid, dissolved in 40 ml of dichloroethane, is then heated for 4 hours under reflux with 10 ml of methanol and 0.5 ml of concentrated $H_2SO_4$. The organic solution is washed with water and dilute bicarbonate, dried, filtered over charcoal and evaporated in vacuo, and the residue is recrystallised from methanol. 19 g (72% yield) of methyl ester, melting at 64°–66° C., are obtained.

(2) CRL 40,258

A solution of hydroxylamine is prepared from 10.5 g (0.15 mol) of hydroxylamine hydrochloride and 10.4 g (0.2 mol) of sodium methylate in 150 ml of methanol. The sodium chloride is filtered off and 22.8 g (0.08 mol) of methyl β-(10-phenothiazinyl)-propionate are added to the filtrate. After 48 hours contact at ambient temperature, the mixture is evaporated to dryness in vacuo. 100 ml of water and 10 ml of concentrated sodium hydroxide solution are added. The product is filtered off cold, washed with 20 ml of iced water and recrystallised from 100 ml of water. CRL 40,258 is obtained in a yield of 56%. Melting point: 155°–160° C. (with decomposition).

EXAMPLE 7

2-(N,N-Diphenylcarbamoyl)-propionohydroxamic acid

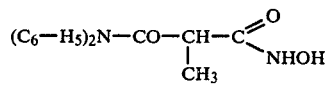

Code No. CRL 40,438

(1) Ethyl 2-(N,N-diphenylcarbamoyl)-propionate

A solution of sodium ethylate is prepared from 1.15 g (0.05 gram atom) of sodium in 25 ml of ethanol, 14.15 g (0.05 mol) of ethyl N,N-diphenylcarbamoyl-acetate are added and thereafter 7.8 g (0.055 mol) of methyl iodide are added dropwise to the solution thus obtained, whilst stirring the latter; the temperature reaches the reflux point at the end of the addition; it is maintained thereat for quarter of an hour, the mixture is evaporated in vacuo, the residue is taken up in ether and the solution is washed with dilute HCl and dilute bicarbonate and then with water. It is dried and evaporated in vacuo, and the residue is crystallised from petroleum ether. The stated ester (melting point=39°–40° C.) is obtained in a yield of 88%.

(2) CRL 40,438

4.9 g (0.125 gram atom) of sodium in small pieces are added to 50 ml of anhydrous methanol and 2/3 of the sodium ethylate solution thus obtained is used to neutralise a solution of 5.25 g (0.075 mol) of hydroxylamine hydrochloride in 50 ml of anhydrous methanol; 15 g (0.05 mol) of ethyl 2-(N,N-diphenylcarbamoyl)-propionate are then added, after which the remaining one-third of the sodium ethylate solution is added in the cold. The reactants are left in contact overnight at 50° C., the mixture is evaporated to dryness in vacuo, the residue is taken up in ether and the sodium salt is filtered off, dissolved in water and acidified with concentrated HCl. CRl 40,438 is obtained by filtering off, drying and recrystallising from acetonitrile. Melting point: 171°–172° C. Yield: 68%.

EXAMPLE 8

2-(N,N-Diphenylcarbamoyl)-butyrohydroxamic acid

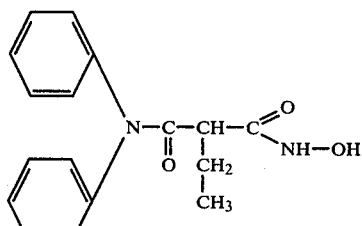

Code No. CRL 40,439

(1) Ethyl 2-(N,N-diphenylcarbamoyl)-butyrate

Method A: A solution of 14.3 g (0.075 mol) of α-ethoxycarbonyl-butyryl chloride in 75 ml of benzene is run dropwise into a stirred solution of 25.5 g (0.15 mol) of diphenylamine in 150 ml of benzene at 20° C. After standing overnight, the diphenylamine hydrochloride is filtered off. The filtrate is washed with dilute HCl, dilute sodium bicarbonate and water. It is dried and evaporated in vacuo, the residue is recrystallised from diisopropyl ether and the stated amide-ester (melting point: 64°–65° C.) is obtained in a yield of 90%.

Method B: A solution of sodium ethylate is prepared from 0.46 g (0.02 gram atom) of sodium in 15 ml of ethanol, and 5.66 g (0.02 mol) of ethyl N,N-diphenylcarbamoyl-acetate are added, followed by 4 g (0.025 mol) of ethyl iodide added dropwise. The mixture is heated for about 2 hours under reflux until the pH is about 7, and is then evaporated to dryness in vacuo, the residue is taken up in 100 ml of ether and this solution is treated as in Example A. The same compound is obtained, in a yield of 88%.

(2) CRL 40,439

A solution of hydroxylamine hydrochloride (7 g; 0.1 mol) in 50 ml of methanol is rendered alkaline with a solution of sodium ethylate prepared from 3.7 g (0.16 gram atom) of sodium in 50 ml of absolute methanol. The mixture is filtered and 18.6 g (0.06 mol) of ethyl 2-(N,N-diphenylcarbamoyl)-butyrate are added to the filtrate. The reactants are left in contact overnight, the alcohol is evaporated in vacuo, the residue is taken up in ether and the sodium salt is filtered off. It is dissolved in water, the solution is acidified with 3 N HCl and the product is filtered off and washed with water. CRL 40,439 is obtained by recrystallisation from acetone. Melting point: 159°–160° C. Yield: 64%.

EXAMPLE 9

N,N-(Dicyclohexyl)-carbamoylacetohydroxamic acid

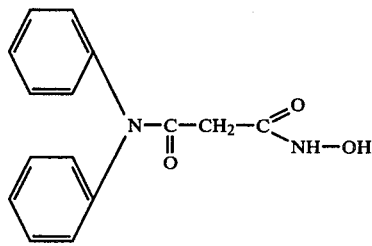

Code No. CRL 40,446

(1) Ethyl N,N-(dicyclohexyl)-carbamoyl-acetate 15 g (0.1 mol) of ethylmalonyl chloride dissolved in 100 ml of anhydrous benzene are run dropwise, whilst stirring, at 25° C., into a solution of 36 g (0.2 mol) of dicyclohexylamine and 200 ml of anhydrous benzene. After leaving the reactants in contact overnight, the mixture is filtered and the filtrate is washed with dilute HCl, dilute sodium bicarbonate and then water. It is dried and evaporated in vacuo, 100 ml of petroleum ether are added and the product is filtered off. 29 g of amido-ester are obtained. Yield: 99%; melting point: 30°–35° C.

(2) CRL 40,446

29 g (0.1 mol) of ethyl N,N-(dicyclohexyl)-carbamoylacetate and 10.5 g (0.15 mol) of hydroxylamine hydrochloride in 200 ml of anhydrous methanol are mixed in the cold and a solution of 5.75 g (0.25 gram atom) of sodium in 100 ml of methanol is added; after leaving the reactants in contact for 18 hours, the mixture is evaporated to dryness in vacuo and the residue is taken up in water and acidified with 3 N HCl. CRL 40,446 is obtained by filtering off, drying and recrystallising from ethanol. Melting point: 198°–200° C. (with decomposition). Yield: 68%.

EXAMPLE 10

2-[3-(5,5-Diphenylhydantoinyl)]-propionohydroxamic acid

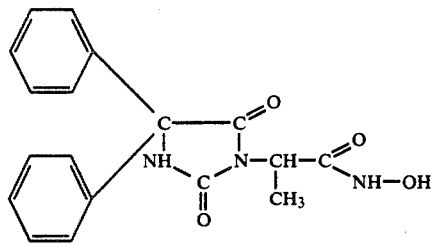

Code No.: CRL 40,447

(1) Ethyl 2-[3-(5,5-diphenylhydantoinyl)]-propionate

A solution of 12.6 g (0.05 mol) of 5,5-diphenylhydantoin and 10 g (0.055 mol) of ethyl 2-bromopropionate in 100 ml of ethanol is heated under reflux. A solution of 1.15 g (0.05 gram atom) of sodium in 100 ml of ethanol is added dropwise over the course of 2 hours, whilst stirring. The mixture is kept under reflux for 1 hour, the ethanol is driven off in vacuo, the residue is taken up in 250 ml of ether and the solution is washed with dilute NaOH and with water. It is dried and evaporated, and the residue is recrystallised from diisopropyl ether. 14.6 g (yield: 83%) of ester, melting at 94°–95° C., are obtained.

(2) CRL 40,447

A solution of 5.25 g (0.075 mol) of hydroxylamine hydrochloride in 150 ml of anhydrous methanol is mixed in the cold with a solution of 2.88 g (0.125 gram atom) of sodium in 75 ml of methanol. The sodium chloride is filtered off and 17.6 g (0.05 mol) of ethyl 2-[3-(5,5-diphenylhydantoinyl)]-propionate are added to the filtrate. After leaving the reactants in contact overnight, the mixture is evaporated to dryness in vacuo, the residue is taken up in 200 ml of water and acidified with 3 N HCl, 50 ml of ether are added and the product is filtered off and washed with water and with ether. CRL 40,447 is obtained by recrystallisation from methanol. Double melting point at 128°–130° C. and 205°–206° C. Yield: 60%.

EXAMPLE 11

3-(5-Ethyl-5-phenyl-hydantoinyl)-acetohydroxamic acid

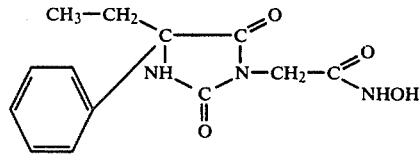

Code No.: CRL 40,450

(1) 5-Ethyl-5-phenyl-hydantoin

A solution of 26.8 g (0.2 mol) of propiophenone, 80 g (0.8 mol) of ammonium carbonate dissolved in 300 ml of water and 28 g (0.4 mol) of potassium cyanide in 300 ml of ethanol is heated under reflux for 8 hours, whilst stirring. The solution is cooled in a mixture of ice and salt; the hydantoin precipitates. The precipitate thus obtained is filtered off and washed with water. 27.1 g (yield: 66%) of 5-ethyl-5-phenyl-hydantoin, melting at 202° C., are obtained.

(2) Ethyl 3-(5-ethyl-5-phenyl-hydantoinyl)-acetate

A solution of 20.4 g (0.1 mol) of 5-ethyl-5-phenyl-hydantoin and 12.2 ml (0.11 mol) of ethyl bromoacetate in 200 ml of anhydrous ethanol is heated under reflux, whilst stirring, and a solution of sodium ethylate prepared from 2.3 g (0.1 gram atom) of sodium and 200 ml of anhydrous ethanol is run in dropwise over the course of 3 hours. The mixture is heated for a further hour and the alcohol is then evaporated. The precipitate obtained is filtered off and then washed with water. 27.2 g (yield: 93%) of ester, melting at 120°–121° C., are obtained.

(3) CRL 40,450

11.6 g (0.04 mol) of the preceding product are mixed with a solution of hydroxylamine prepared from 4.2 g (0.06 mol) of hydroxylamine hydrochloride in 100 ml of methanol and 2.3 g (0.1 gram atom) of sodium in 100 ml of methanol. After leaving the reactants in contact overnight at 20° C., the mixture is evaporated to dryness in vacuo, 100 ml of water are added and the mixture is filtered. The solution is acidified with 3 N HCl and the organic phase is extracted with ethyl acetate after which the latter is evaporated. An oil is obtained, which is dissolved in the minimum amount of ethyl acetate whilst heating gently, the solution is cooled and the product is filtered off and washed with ethyl acetate. After suction-draining and recrystallisation from ethanol, CRL 40,450 is obtained. Melting point: 201°–202° C. Yield: 43%.

EXAMPLE 12

N-(4-Chlorophenyl)-carbamoyl-acetohydroxamic acid

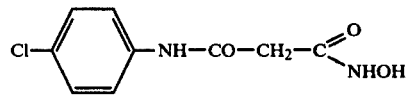

Code No. CRL 40,464

(1) Ethyl N-(4-chlorophenyl)-carbamoylacetate

A solution of 7.5 g (0.05 mol) of ethylmalonyl chloride in 25 ml of anhydrous benzene is run dropwise, whilst stirring, into a solution of 12.7 g (0.1 mol) of 4-chloroaniline and 100 ml of anhydrous benzene. Stirring is continued for 2 hours at ambient temperature and the precipitate of 4-chloroaniline hydrochloride is filtered off. The filtrate is evaporated to dryness in vacuo and the residue is taken up in diisopropyl ether and filtered off. 11.5 g are obtained. Yield 95% of the stated product. Melting point: 82° C.

(2) CRL 40,464

A solution containing 3.5 g (0.05 mol) of hydroxylamine hydrochloride, 0.1 mol of sodium methylate and 12.1 g (0.05 mol) of ethyl N-(4-chlorophenyl)-carbamoylacetate is left standing for 4 hours at 20° C. The mixture is evaporated to dryness in vacuo, the residue is taken up in 100 ml of water and the solution is filtered and acidified with 3 N HCl. The product is filtered off, washed with water and dried. Recrystallisation from 95% strength ethanol gives CRL 40,464. Melting point: 212°–213° C. (with decomposition). Yield: 82%.

EXAMPLE 13

3,4-Dichlorobenzylsulphinyl-acetohydroxamic acid

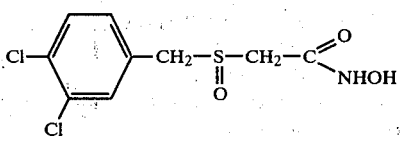

Code No. CRL 40,465

(1) 3,4-Dichlorobenzylthioacetic acid

A mixture of 19.5 g (0.1 mol) of 3,4-dichlorobenzyl-chloride and 7.6 g (0.1 mol) of thiourea in 50 ml of water are heated under reflux for 30 minutes with stirring, and then a solution of 16 g (0.4 mol) of NaOH in 25 ml of water is run in at 60°–70° C.; the mixture is heated under reflux for 15 minutes, a solution of 15 g (0.15 mol) of chloroacetic acid, 7 g of sodium carbonate and 50 ml of water is run in at 60°–70° C., and the mixture is maintained under reflux for 1 hour. The mixture is acidified cold with concentrated HCl, extracted with ether, and the extract is washed with water, dried and evaporated. The residue is taken up in petroleum ether and filtered off. 21 g of the stated product are obtained (yield: 83%) melting point: 63°–64° C.

(2) 3,4-Dichlorobenzylthioaceto-hydroxamic acid 20.2 g (0.08 mol) of 3,4-dichlorobenzylthioacetic acid are esterified with 10 ml of methanol, 0.6 ml of concentrated $H_2SO_4$ and 100 ml of dichloroethane. The mixture is heated under reflux for 4 hours, washed with water and with dilute bicarbonate solution, and dried. The mixture is evaporated in vacuo. The oily residue, in methanol, is treated with a solution of hydroxylamine (0.1 mol) in the presence of 0.18 mol of sodium methylate. After leaving the reactants in contact overnight, the mixture is evaporated to dryness in vacuo, the residue is taken up in water, the mixture is filtered over charcoal and the filtrate is precipitated with 3 N HCl, the product is extracted with ether, the extract is dried and evaporated and the product is crystallised in diisopropyl ether. 15 g of the stated product are obtained (yield 71%). Melting point: 75°–76° C.

(3) CRL 40,465

14.6 g (0.055 mol) of the above product in 50 ml of $CH_3CO_2H$ are oxidised with 5.2 ml of 130 volumes strength $H_2O_2$. After 1 hour at 45°–50° C., the product is filtered off and washed with ether. CRL 40,465 is obtained by recrystallisation from dioxane. Yield 55%. Melting point: 191°–192° C.

EXAMPLE 14

2-(p-Chlorobenzylsulphinyl)-propionohydroxamic acid

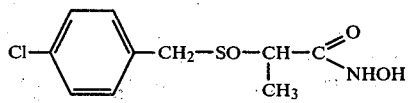

Code No. CRL 40,466

(1) Ethyl 2-(p-chlorobenzylthio)-propionate

A mixture of 19.5 ml (0.15 mol) of 4-chlorobenzyl-mercaptan, 27.1 g (0.15 mol) of ethyl α-bromopropionate, 21 g of potassium carbonate and 0.1 g of potassium iodide in 100 ml of anhydrous acetone is kept under reflux for 6 hrs. It is filtered, the precipitate is washed with acetone and the filtrate is evaporated in vacuo. 200 ml of ether are added to the residue and the mixture is washed with dilute NaOH, dilute HCl and water, dried and evapoated in vacuo.

(2) 2-(p-Chlorobenzylthio)-propionohydroxamic acid 10.5 g (0.15 mol) of hydroxylamine hydrochloride are treated with a solution of sodium methylate prepared with 5.75 g (0.25 gram atom) of sodium in 200 ml of methanol. The sodium chloride is filtered off and 25.85 g (0.1 mol) of ethyl 2-(p-chlorobenzylthio)-propionate are added to the filtrate. After leaving the reactants in contact overnight, the mixture is evaporated in vacuo, the residue is taken up in 200 ml of water, the mixture is filtered, the filtrate is precipitated with 3 N HCl, the product is filtered off, washed with water and dried, and 20.2 g (yield: 82%) of the stated hydroxamic acid are obtained. Melting point: 104°–105° C.

(3) CRL 40,466

19.6 g (0.08 mol) of the preceding product, dissolved in 75 ml of acetic acid, are oxidised with 8 ml of hydrogen peroxide of 110 volumes strength, the mixture is kept at 50° C. for 1 hour and is evaporated to dryness in vacuo, the residue is taken up in 100 ml of ethyl acetate and the product is filtered off. Recrystallisation from acetone and from ethanol gives CRL 40,466, which is in the form of a salmon-coloured powder. Melting point: 132°–133° C. Yield: 58%.

EXAMPLE 15

On proceeding as indicated in Example 2, but replacing 5,5-diphenyl-hydantoin by 5,5-di-(p-chlorophenyl)-hydantoin (melting point: 319°–320° C.), ethyl 3-(5,5-di-p-chlorophenylhydantoinyl)-acetate (melting point: 145° C.) and 3-(5,5-di-p-chlorophenyl-hydantoinyl)-acetohydroxamic acid (Code No. CRL 40,468), melting point: 139°–141° C., are successively obtained.

EXAMPLE 16

5-(10,11-Dihydro-dibenz[b,f]azepino)-carbonylacetohydroxamic acid

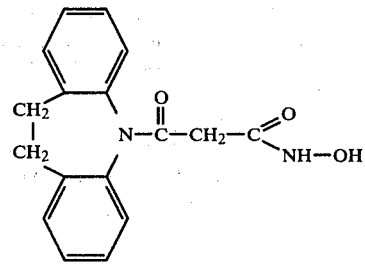

Code No. CRL 40,471

9.8 g (0.05 mol) of iminodibenzyl and 7.5 g (0.05 mol) of ethylmalonyl chloride are mixed in 100 ml of benzene at 20° C., the mixture is stirred under a stream of nitrogen for 16 hours and is washed with dilute bicarbonate and water, then dried, and filtered over charcoal. It is evaporated in vacuo and the oily product thus obtained, which is ethyl 5-(10,11-dihydro-dibenz[b,f]azepino)-carbonyl-acetate, is treated with a solution of hydroxylamine prepared from 3.5 g (0.05 mol) of hydroxylamine hydrochloride, 2.3 g of sodium and 200 ml of methanol. After leaving the reactants in contact overnight, the methanol is evaporated in vacuo, the residue is taken up in 150 ml of water, the mixture is filtered over charcoal and the acid is precipitated with 3 N HCl, filtered off and dried. Recrystallisation from methanol gives CRL 40,471, which is in the form of a salmon-coloured powder. Melting point: 201°–202° C. (with decomposition). Yield: 76%.

EXAMPLE 17

4-Amino-phenylcarbamoyl-acetohydroxamic acid hydrochloride

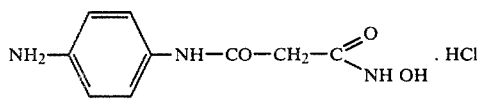

Code No. CRL 40,472

(1) Ethyl 4-nitro-phenylcarbamoylacetate

A solution of 15 g (0.1 mol) of ethylmalonyl chloride in 50 ml of methylene chloride is added dropwise to a refluxing solution of 27.6 g (0.2 mol) of p-nitroaniline in 200 ml of methylene chloride. After standing overnight, the precipitate of para-nitroaniline hydrochloride is filtered off, the filtrate is evaporated to dryness, the residue is taken up in diisopropyl ether and the product is filtered off and recrystallised from ethyl acetate. 22 g (87% yield) of the stated product, melting at 102°–103° C., are obtained.

(2) Ethyl 4-amino-phenylcarbamoylacetate 25.5 g (0.1 mol) of the preceding product in solution in 250 ml of ethanol are reduced with hydrogen in the presence of a catalyst (2 g of palladium on charcoal). The catalyst is filtered off, the filtrate is evaporated in vacuo the residue is taken up in diisopropyl ether, the product is filtered off and 21.5 g (97% yield) of the stated amino-ester melting at 58°–59° C., are obtained.

(3) CRL 40,472

A mixture of 17.8 g (0.08 mol) of ethyl 4-aminophenylcarbamoylacetate, 7 g (0.1 mol) of hydroxylamine hydrochloride and 4.6 g (0.2 gram atom) of sodium in 250 ml of anhydrous methanol is left in contact for 2 hours at 20° C. The methanol is evaporated in vacuo, the residue is taken up in 100 ml of water and acidified with 5 N HCl and the product is filtered off. Recrystallisation from 80 ml of water gives CRL 40,472. Melting point 164°–165° C. (with decomposition). Yield: 64%.

EXAMPLE 18

4-Amino-benzamido-acetohydroxamic acid hydrochloride

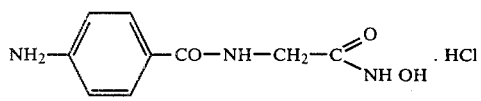

Code No. CRL 40,473

(1) Ethyl 4-amino-benzamidoacetate 17.6 g (0.07 mol) of ethyl 4-nitro-benzamidoacetate dissolved in 250 ml of ethanol are hydrogenated in the presence of a catalyst (2 g of palladium on charcoal); the catalyst is filtered off, the filtrate is evaporated to dryness in vacuo, the residue is taken up in 100 ml of diisopropyl ether and the product is filtered off. 15 g (87% yield) of the stated product are obtained. Melting point: 93°–94° C.

(2) CRL 40,473

5.75 g (0.25 gram atom) of sodium are added in small pieces to 150 ml of anhydrous methanol, and this cold solution of sodium methylene is then poured into a solution of 10.5 g (0.15 mol) of hydroxylamine hydrochloride in 100 ml of anhydrous methanol. The mixture is stirred for half an hour in the cold, the sodium chloride precipitate is filtered off and 22.2 g (0.1 mol) of ethyl 4-aminobenzamidoacetate are added to the filtrate; after leaving the reactants in contact overnight, the mixture is evaporated to dryness in vacuo, the residue is taken up in 100 ml of water and the hydrochloride is precipitated by adding 6 N HCl up to pH=1, and is filtered off and washed with 10 ml of cold water. CRL 40,473 is thus obtained by recrystallisation from a 4:1 (volume/volume) mixture of methanol and water. Melting point 182°–185° C. (with decomposition). Yield: 72%.

EXAMPLE 19

α-Naphthylmethylene-sulphinyl-acetohydroxamic acid

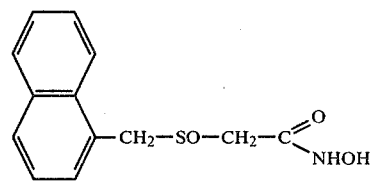

Code No. CRL 40,475

(1) α-Naphthylmethylene-thioacetic acid

A solution of 15.2 g (0.2 mol) of thiourea in 100 ml of water is introduced into a 1 liter three-necked flask equipped with a magnetic stirrer, a condenser and a dropping funnel, and 35.3 g (0.2 mol) of α-chloromethylnaphthalene are added all at once, at 50°–60° C. The mixture is heated until it reaches the refluxing temperature and is kept at the boil for quarter of an hour. The thiouronium salt precipitates. The mixture is then cooled and a solution of 32 g of sodium hydroxide (0.8 mol) in 50 ml of water is then added dropwise at about 60° C. The resulting mixture is heated under reflux until the solution becomes limpid and is then cooled, and a solution of about 0.28 mol of sodium chloracetate (obtained by neutralising 26.36 g of chloroacetic acid with 23.52 g of sodium bicarbonate in 200 ml of water) is (then) added dropwise at 60°–70° C. The whole is then heated under reflux for half an hour after which it is cooled and acidified in the cold by adding 3 N HCl, thus precipitating α-naphthylmethylene-thioacetic acid, which is filtered off. 44.5 g of product are collected (yield: 95%). Instantaneous melting point=102°–103° C.

(2) Ethyl α-naphthylmethylene-thioacetate 19.72 g (0.085 mol) of the preceding product are dissolved in 160 ml of 1,2-dichloroethane, and 16 ml of anhydrous ethanol and 1.6 ml of concentrated sulphuric acid are added. The mixture is heated under reflux for at least 2 hours and is then cooled, and the organic phase is decanted, the water formed being removed, and washed with a dilute sodium hydroxide solution and then with water. It is dried over MgSO₄ and the solvent is evaporated. 19.8 g of ethyl α-naphthylmethylene-thioacetate [overall yield=89%] are thus collected, this product being in the form of a limpid orange-coloured oil.

(3) α-Naphthylmethylene-thio-acetohydroxamic acid

The ester obtained above (0.076 mol), diluted with 50 ml of methanol, is added to a solution of hydroxylamine prepared from 7.92 g (0.114 mol) of hydroxylamine hydrochloride in 190 ml of methanol and 4.37 g (0.19 gram atom) of sodium in 190 ml of anhydrous methanol. After leaving the reactants in contact overnight at 20° C., the methanol is evaporated, the residue is taken up in water (alkaline medium), the mixture is filtered over charcoal, the filtrate is acidified by adding 3 N HCl and α-naphthylmethylene-thio-acetohydroxamic acid is thus precipitated; this acid is filtered off, washed with water and then with ether and dried, and after recrystallisation from ethyl acetate 11.2 g ( 0.0453 mol) of product (overall yield=59%) are collected. Instantaneous melting point=129°-130° C.

(4) CRL 40,475

9 g (0.0364 mol) of the preceding product are introduced into a flask and 100 ml of acetic acid and 3.64 ml of $H_2O_2$ (about 110 volumes strength) are added. The mixture is left at 40°-45° C. for about 1 and a half hours; white crystals appear gradually. The precipitate obtained is filtered off, washed with water and then redissolved in a dilute sodium hydroxide solution, and the solution is filtered and acidified with 3 N HCl. This precipitates α-naphthylmethylene-sulphinylacetohydroxamic acid. 8.4 g of this product are collected after filtration. Melting point: 209°-210° C. Yield=87%.

EXAMPLE 20

2-(1-Phenyl-benzimidazolyl)-acetohydroxamic acid

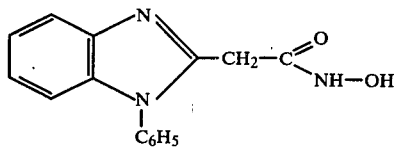

Code No. CRL 40,490

(1) Ethyl 2-(1-phenyl-benzimidazolyl)-acetate

A solution of 11.75 g (0.064 mol) of ortho-aminodiphenylamine in 90 ml of ethanol is stirred at 20° C. and 12.5 g (0.064 mol) of ethyl ethylcarboximino-acetate hydrochloride are added. After leaving the reactants in contact for 2 hous, the ammonium chloride formed is filtered off and the filtrate is evaporated in vacuo. The residue is taken up in ether, the solution is washed with water and dried, the ether is evaporated and the residue is crystallised from petroleum ether, filtered off and recrystallised from diisopropyl ether. 16 g (89% yield) of the stated ester, melting at 84° C., are obtained.

(2) CRL 40,490

A solution of hydroxylamine is prepared from 3.5 g (0.05 mol) of hydroxylamine hydrochloride in 50 ml of anhydrous methanol and 2.3 g (0.1 gram atom) of sodium in 50 ml of anhydrous methanol. The sodium chloride formed is filtered off and 14 g (0.05 mol) of ethyl 2-(1-phenylbenzimidazolyl)-acetate are added to the filtrate, and the reactants are left in contact overnight. The mixture is evaporated to dryness in vacuo, the residue is taken up in water, the solution is neutralised with 3 N HCl and the product is filtered off, washed with water and dried. Recrystallisation from methanol gives CRL 40,490. Melting point: 212°-215° C. (with decomposition) Yield: 68%

EXAMPLE 21

3,4-Dichlorophenylcarbamoylacetohydroxamic acid

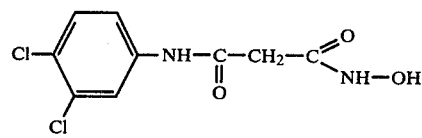

Code No. CRL 40,491

(1) Ethyl 3,4-dichlorophenylcarbamoylacetate

A solution of 15 g (0.1 mol) of ethylmalonyl chloride in 100 ml of methylene chloride is run dropwise into a solution, which is stirred at 20° C., of 32.4 g (0.2 mol) of 3,4-dichloroaniline and 200 ml of methylene chloride; the mixture is stirred for a further 2 hours and the precipitate of 3,4-dichloroaniline hydrochloride is filtered off. The filtrate is evaporated to dryness in vacuo and the residue is recrystallised from diisopropyl ether. 24.5 g (89% yield) of the stated product, melting at 74°-75° C., are obtained.

(2) CRL 40,491

A solution of sodium methylate is prepared from 3.7 g (0.16 gram atom) of sodium and 100 ml of anhydrous methanol and this solution is added, in the cold, to a solution of 5.6 g (0.08 mol) of hydroxylamine hydrochloride and 100 ml of anhydrous methanol. The sodium chloride formed is filtered off and 22 g (0.078 mol) of ethyl 3,4-dichlorophenylcarbamoylacetate are added to the filtrate. The reactants are left in contact overnight, the mixture is evaporated to dryness in vacuo, the residue is taken up in water, the solution is acidifed with 3 N HCl and the product is filtered off and dried. Recrystallisation from ethanol gives CRL 40,491. Melting point=201-202° C. Yield: 62%.

EXAMPLE 22

(3,4-Dichloroanilino)-acetohydroxamic acid

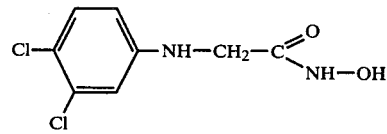

Code No. CRL 40,500

(1) (3,4-Dichloroanilino)-acetic acid

A solution of 32.4 g (0.2 mol) of 3,4-dichloroaniline and 28 g (0.2 mol) of sodium acetate in 200 ml of acetic acid and 40 ml of water is stirred under reflux. A solution of 28.5 g (0.3 mol) of chloroacetic acid and 15.9 g (0.15 mol) of sodium carbonate in 100 ml of water is run in over the course of half an hour. The mixture is kept under reflux for 3 hours, 30 ml of concentrated hydrochloric acid are added and the acetic acid is evaporated in vacuo. The residue is taken up in ether, the solution is washed with water and the acid is extracted with dilute sodium bicarbonate, reprecipitated with 3 N HCl, filtered off and dried. 27.2 g (62% yield) of acid, melting at 128°-130° C., are obtained.

(2) Ethyl (3,4-dichloranilino)-acetate

A solution of 27.5 g (0.125 mol) of 3,4-dichloroanilinoacetic acid, 190 ml of dichloroethane, 15 ml (0.2 mol) of ethanol and 1.5 ml of concentrated $H_2SO_4$ is heated for 4 hours under reflux. It is washed with water and with dilute sodium bicarbonate, dried and evaporated to dryness in vacuo. The ester is recrystallised from ethanol and is obtained in a yield of 78%. It melts at 103°–104° C.

(3) CRL 40,500

A solution of sodium methylate, that is to say 3.22 g (0.14 gram atom) of sodium in 75 ml of methanol is mixed in the cold with 4.9 g (0.07 mol) of hydroxylamine hydrochloride in solution in 100 ml of methanol, the sodium chloride is filtered off and 16.1 g (0.065 mol) of ethyl 3,4-dichloroanilinoacetate are added to the filtrate. The reactants are left in contact overnight, the mixture is evaporated to dryness in vacuo, the residue is taken up with water, the solution is filtered over charcoal and the product is precipitated with 3 N HCl and filtered off. Recrystallisation from ethyl acetate gives CRL 40,500. Melting point=138°–140° C. (with decomposition). Yield: 36%.

EXAMPLE 23

3,4,5-Trimethoxyphenyl-carbamoyl-acetohydroxamic acid

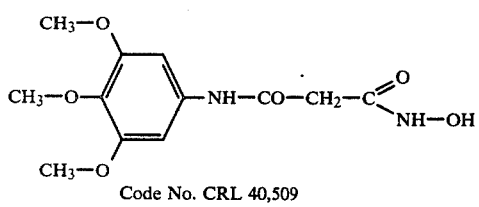

Code No. CRL 40,509

(1) Ethyl 3,4,5-trimethoxyphenyl-carbamoylacetate

A solution of 7.5 g of ethylmalonyl chloride in 50 ml of anhydrous benzene is run, under reflux, into a solution of 18.3 g (0.1 mol) of 3,4,5-trimethoxyaniline in 150 ml of anhydrous benzene. After refluxing for 1 hour the mixture is cooled and the precipitate is filtered off and washed with twice 50 ml of ether. The filtrate is washed with dilute HCl and water, dried and evaporated, and the residue is recrystallised from a 1:1 ( volume/volume) mixture of ethyl acetate and diisopropyl ether. 12 g (80% yield) of the stated product, melting at 93° C., are obtained.

(2) CRL 40,509

4.15 g (0.18 gram atom) of sodium are added in small pieces to 100 ml of anhydrous methanol and this cold solution is then poured into a solution of 7 g (0.1 mol) of hydroxylamine hydrochloride in 100 ml of methanol; the sodium chloride is filtered off and 23.8 g (0.08 mol) of ethyl 3,4,5-trimethoxyphenylcarbamoylacetate are added to the filtrate. The reactants are left in contact overnight, the mixture is evaporated to dryness in vacuo, the residue is taken up in water, the solution is acidified with 3 N HCl and the product is filtered off and washed with cold water and with diisopropyl ether. Recrystallisation from methanol gives CRL 40,509. Melting point=195°–196° C. (with decomposition). Yield: 49%.

EXAMPLE 24

3-Trifluoromethylphenyl-carbamoyl-acetohydroxamic acid

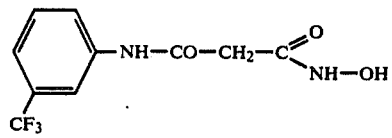

Code No. CRL 40,512

On proceeding as indicated in Example 23, but replacing the 3,4,5-trimethoxyaniline by 3-trifluoromethylaniline, the following are obtained:

(1) ethyl 3-trifluoromethylphenyl-carbamoyl-acetate (melting point=67° C.), and (2) CRL 40,512 (melting point=206°–207° C., with decomposition), for which the recrystallisation solvent is ethanol.

EXAMPLE 25

2,6-Dichlorophenyl-carbamoyl-acetohydroxamine acid

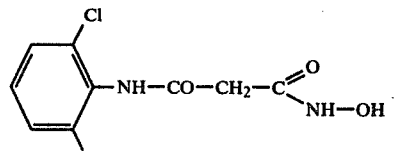

Code No. CRL 40,510

On proceeding as indicated in Example 23, but replacing the 3,4,5-trimethoxyaniline by 2,6-dichloroaniline, the following are obtained:

(1) ethyl 2,6-dichlorophenyl-carbamoyl-acetate (melting point=115°–116° C.) and (2) CRL 40,510 (melting point=175°–176° C., with decomposition), for which the recrystallisation solvent is a mixture of ethanol and diisopropyl ether.

EXAMPLE 26

5-Phenylureidoacetohydroxamic acid

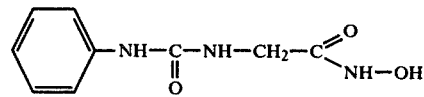

Code No. CRL 40,513

(1) Ethyl 5-phenylureidoacetate

A solution of 17.6 g (0.17 mol) of ethyl aminoacetate in 200 ml of anhydrous benzene is stirred and 21 g (19 ml—0.175 mol) of phenyl isocyanate are added dropwise whilst keeping the temperature below 40° C. The mixture is stirred for a further 2 hours at 20° C. and is left overnight. The product is filtered off, washed with diisopropyl ether and dried, and 26.6 g (71% yield) of the stated product, melting at 110°–111° C., are obtained.

(2) CRL 40,513

22.2 g (0.1 mol) of the preceding product are treated with a hydroxylamine solution prepared from 7.7 g (0.11 mol) of hydroxylamine hydrochloride, 5.07 g of sodium and 200 ml of methanol. After leaving the reactants in contact for 3 hours, the mixture is evaporated to dryness in vacuo, the residue is taken up in 300 ml of water and the solution is acidified in the cold with 3 N HCl. The product is filtered off, washed with water and with diisopropyl ether and dried. Recrystallisation from ethanol gives CRL 40,513. Melting point = 165°–166° C. Yield: 57%.

EXAMPLE 27 p-Fluorobenzylsulphinyl-acetohydroxamic acid

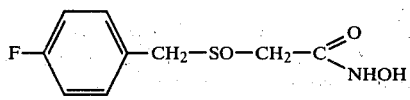

Code No. CRL 40,511

(1) p-Fluorobenzylthioacetic acid

A solution of 15.2 g (0.2 mol) of thiourea in 100 ml of water is introduced into a 1 liter 3-necked flask equipped with a magnetic stirrer, a condenser and dropping funnel, and 28.9 g (0.2 mol) of p-fluorobenzylchloride are introduced, at 50°–60° C., in a single operation. The mixture is heated to reflux and boiling is maintained for about 15 minutes; the solution becomes limpid. Thereafter the mixtuure is cooled and a solution of 32 g (0.8 mol) of NaOH in water is added dropwise at about 60° C. The whole is heated under reflux for about 30 minutes and cooled and a solution of about 0.28 mol of sodium chloroacetate (obtained by neutralising 26.46 g of chloracetic acid in 200 ml of water with 23.52 g of sodium bicarbonate) is added dropwise at 60°–70° C. Thereafter the whole is heated under reflux for 30 minutes, and then cooled. The mixture is acidified with 3 N HCl, the oil obtained is taken up in methylene chloride, the solution is washed with a dilute solution of sodium bicarbonate, filtered over charcoal and acidified once with 3 N HCl and p-fluorobenzylthioacetic acid thus precipitates and is filtered off. After recrystallisation from cyclohexane, 33.4 g (yield: 83%) of the said acid are collected. Instantaneous melting point: 68°–69° C.

(2) Ethyl p-fluorobenzylthioacetate 17 g (0.085 mol) of the acid obtained above are dissolved in 160 ml of 1,2-dichloroethane, 16 ml of anhydrous ethanol and 1.6 ml of concentrated $H_2SO_4$ are added. The whole is heated under reflux for about 6 hours and cooled, the organic phase is decanted and the water which has formed is removed, and the solution is washed with a dilute solution of sodium bicarbonate and then with water. Thereafter the solution is dried over $Na_2SO_4$ and the solvent evaporated off. 17.4 g of a yellow oil are thus collected: this is ethyl p-fluorobenzylthioacetate (overall yield: 89%).

(3) p-Fluorobenzylthioacetohydroxamic acid

The ester obtained above (0.0763 mol) is added to a solution of hydroxylamine prepared from 7.92 g (0.114 mol) of hydroxylamine hydrochloride in 190 ml of methanol and 4.37 g of sodium in 190 ml of anhydrous methanol. After leaving the reactants in contact overnight at ambient temperature, the methanol is evaporated, the residue is taken up in water, the solution is filtered over charcoal and acidified with 3 N HCl; p-fluorobenzylthioacetohydroxamic acid thus precipitates, and is filtered off and washed with water. 11.2 g (yield: 68%) of the said acid are collected. Instantaneous melting point: 115°–116° C.

(4) CRL 40,511

7.5 g (0.0349 mol) of the hydroxamic acid obtained above are introduced into a flask, and 35 ml of acetic acid and 3.8 ml of $H_2O_2$ (110 volumes strength) are added. The constituents of the mixture are left in contact for about 3 hours at ambient temperature; white crystals appear. These are filtered and washed with diisopropyl ether. After recrystallisation from methanol, 6.65 g of p-fluorobenzylsulphinylacetohydroxamic acid are obtained. Yield: 83%. Instantaneous melting point: 176°–177° C.

EXAMPLE 20 p-Methoxybenzyl-sulphinyl-acetohydroxamic acid

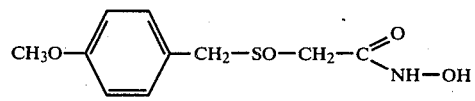

Code No. CRL 40,498

(1) p-Methoxybenzylthio-acetic acid

A solution of 18.24 g (0.24 mol) of thiourea in 104 ml of 48% strength hydrobromic acid and 20 ml of water is introduced into a 1 liter three-necked flask equipped with a magnetic stirrer and a condenser. The mixture is heated at 60° C. and 27.6 g (0.2 mol) of p-methoxybenzyl alcohol are introduced. The temperature is raised to 95° C. and the mixture is then allowed to cool. Crystals of thiouronium salt appear; these are filtered off and suction-drained. The precipitate obtained above is introduced into a 500 ml three-necked flask together with 60 ml of NaOH. The mixture is heated to 70° C. and a solution of 15.6 g (0.0164 mol) of chloroacetic acid dissolved in 30 ml of water is added dropwise. The whole is then heated under reflux for half an hour, after which it is cooled. The mixture is acidified with 3 N HCl, the oil obtained is taken up in methylene chloride and washed with a dilute sodium bicarbonate solution and (?the aqueous phase) is filtered over charcoal and again acidified with 3 N HCl to precipitate p-methoxybenzylthioacetic acid. 25.7 g (60% yield) of the said acid (melting point = 60° C.) are collected.

(2) Ethyl p-methoxybenzylthio-acetate 24 g (0.112 mol) of the acid obtained above are dissolved in 210 ml of 1,2-dichloroethane and 22 ml of anhydrous ethanol and 2.2 ml of concentrated sulphuric acid are added. The whole is heated under reflux for about 6 hours and is cooled and the organic phase is decanted, the water formed being removed, and is washed with a dilute sodium bicarbonate solution and then with water. The solution is then dried over $Na_2SO_4$ and the solvent is evaporated. 26.5 g of a limpid yellow oil are thus collected; this is ethyl p-methoxybenzylthio-acetate (overal yield: 96%).

(3) p-Methoxybenxylthio-acetohydroxamic acid

The preceding product (0.110 mol) diluted with 50 ml of methanol is added to a solution of hydroxylamine prepared from 11.63 g (0.165 mol) of hydroxylamine hydrochloride in 275 ml of methanol and 6.32 g of sodium in 275 ml of anhydrous methanol. After leaving the reactants in contact overnight at ambient temperature, the methanol is evaporated, the residue is taken up in water and the solution is filtered over charcoal and acidified with 3 N HCl in order thus to precipitate the p-methoxy-benzylthioacetohydroxamic acid. After filtering off and washing with water, 19.1 g (77% yield) of the said acid (instantaneous melting point = 107° C.) are collected.

(4) CRL 40,498

15.89 g (0.07 mol) of the hydroxamic acid obtained above are introduced into a flask and 70 ml of acetic acid and 7.5 ml of H₂O₂ (about 110 volumes strength) are added. The mixture is left in contact for about 2 hours at ambient temperature; white crystals appear gradually. The precipitate obtained is filtered off and washed with diisopropyl ether. After recrystallisation from methanol, 10 g of p-methoxybenzyl-sulphinyl-acetohydroxamic acid are collected. Instantaneous melting point = 160° C. Yield: 60%.

EXAMPLE 29

2,4-Dichlorobenzylsulphinyl-acetohydroxamic acid

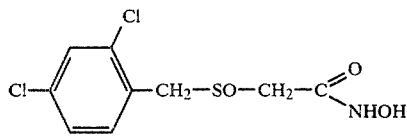

Code No. CRL 40,515

(1) 2,4-Dichlorobenzylthio-acetic acid 15.2 g (0.2 mol) of thiourea in 100 ml of water are introduced into a 1 liter 3-necked flask. The mixture is heated to 50°–60° C. and 39.1 g (0.2 mol) of 2,4-dichlorobenzylchloride are introduced in a single operation. The mixture is heated under reflux and boiling is maintained for 15 minutes; the solution becomes limpid. The mixture is cooled and a solution of 32 g (0.8 mol) of NaOH in 50 ml of water is introduced dropwise at about 60° C. The mixture is again heated under reflux for 30 minutes, cooled and a solution of about 0.28 mol of sodium chloroacetate (obtained by neutralising 26.46 g of chloroacetic acid in 200 ml of water with 23.52 g of NaHCO₃) is introduced, dropwise, at 60°–70° C. The whole is then heated under reflux for 30 minutes, cooled, filtered and acidified with 3 N HCl; the precipitate obtained is filtered off and redissolved cold in dilute sodium bicarbonate solution, and this solution is washed with methylene chloride, filtered and again acidified. 41.7 g (yield: 83%) of product are thus collected. Instantaneous melting point: 72°–73° C.

(2) Ethyl 2,4-dichlorobenzylthio-acetate 37.65 g (0.15 mol) of the above acid are dissolved in 283 ml of 1,2-dichloroethane and 28.5 ml of anhydrous ethanol and 2.9 ml of concentrated H₂SO₄ are added. The whole is heated under reflux for about 6 hours and then cooled, the organic phase is decanted and the water which has formed is removed, and the organic phase is washed with a dilute solution of sodium bicarbonate and then with water. Thereafter the solution is dried over Na₂SO₄ and the solvent evaporated. 43.6 g of a yellow oil are thus collected: this is ethyl 2,4-dichlorobenzylthio-acetate (overall yield: 90%).

(3) 2,4-Dichlorobenzylthio-acetohydroxamic acid

The above ester (0.156 mol) is added to a solution of hydroxylamine prepared from 16.38 g (0.235 mol) of hydroxylamine hydrochloride in 300 ml of methanol and 9 g (0.391 gram atom) of sodium in 300 ml of anhydrous methanol. After leaving the reactants in contact overnight at ambient temperature, the methanol is evaporated, the residue is taken up in water and the solution is filtered over charcoal and acidified with 3 N HCl in order to precipitate 2,4-dichlorobenzylthio-acetohydroxamic acid which is filtered off and washed with water. 28 g (yield: 67%) of the said acid are collected. Instantaneous melting point: 116° C.

(4) CRL 40,515

24 g (0.09 mol) of the above hydroxamic acid are introduced into a flask, and 90 ml of acetic acid and 11 ml of H₂O₂ (110 volumes strength) are added. The mixture is left in contact for about 4 hours at ambient temperature; white crystals appear. These are filtered off, washed with diisopropyl ether, dried and redissolved in a dilute solution of NaOH. The alkaline solution obtained is filtered over charcoal and acidified with 3 N HCl, in order to precipitate 2,4-dichlorobenzylsulphinylacetohydroxamic acid. After filtering, 24 g of CRL 40,515 are collected. Yield: 94%. Instantaneous melting point: 204°–205° C.

EXAMPLE 30

2,6-Dichlorobenzylsulphinyl-acetohydroxamic acid

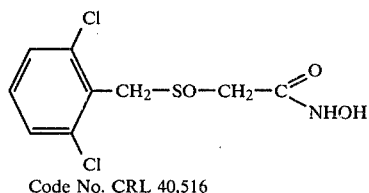

Code No. CRL 40,516

By preceeding as indicated in Example 29, but replacing the 2,4-(Cl₂)C₆H₃CH₂Cl by 2,6-(Cl₂)C₆H₃CH₂Cl, the following products are successively obtained:

(1) 2,6-dichlorobenzylthio-acetic acid (yield 83%; instantaneous melting point: 81°–82° C.), (2) ethyl 2,6-dichlorobenzylthio-acetate (yield 89%) which is in the form of a yellow oil, (3) 2,6-dichlorobenzylthio-acetohydroxamic acid (yield 71%; instantaneous melting point: 124° C.) and (4) CRL 40,516 (22.1 g), after recrystallisation from a 1:1 (volume/volume) mixture of H₂O and CH₃CH₂OH. Yield 78%. Instantaneous melting point: 201° C.

EXAMPLE 31

4-Nitrobenzylsulphinyl-acetohydroxamic acid

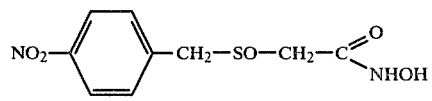

Code No. CRL 40,539

(1) Ethyl 4-nitrobenzylthioacetate 43.2 g (0.2 mol) of p-nitrobenzylbromide, 200 ml of acetone, 0.2 g of potassium iodide, 24 ml of ethyl thioglycolate (namely a slight excess) and 27.6 g (0.2 mol) of potassium carbonate are successively introduced into a 1 liter 3-necked flask. The mixture is heated under reflux for about 4 hours until the bromine derivative completely disappears; the acetone is evaporated, the oil obtained is taken up in ether and in water, the ether phase is washed with a dilute solution of NaOH to remove the excess thiol, and then with a dilute solution of HCl, the solution is dried over Na₂SO₄ and the solvent is evaporated off. 49 g (yield: 95%) of the stated product, which is in the form of an orange coloured oil, are obtained.

(2) 4-Nitrobenzylthio-acetohydroxamic acid

The above ester (0.156 mol) diluted in 50 ml of methanol is added to a solution of hydroxylamine prepared from 16.38 g (0.235 mol) of hydroxylamine hydrochloride in 300 ml of methanol and 9 g (0.391 gram atom) of sodium in 300 ml of anhydrous methanol. The whole is left in contact overnight at ambient temperature, the sodium chloride formed is filtered off, the reaction mixture is acidified directly, the solvent is evaporated, and the precipitate obtained is taken up in water and filtered off. After recrystallisation from isopropyl alcohol, 27 g of p-nitrobenzylthio-acetohydroxamic acid are obtained (instantaneous melting point: 118°–119° C.; yield: 72%).

(3) CRL 40,539

18.15 g (0.075 mol) of the above hydroxamic acid are introduced into a flask, and 75 ml of acetic acid and 8 ml of $H_2O_2$ (110 volumes strength) are added. The mixture is left in contact for about 2 hours at ambient temperature; white crystals appear very rapidly, and these are filtered and dried. After recrystallisation from dimethylformamide, 15 g of CRL 40,539 acid are collected. Instantaneous melting point: 227° C. Yield: 77%.

EXAMPLE 32

3,4-Methylenedioxybenzyl-sulphinyl-acetohydroxamic acid

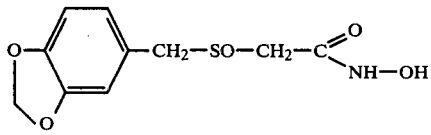

Code No. CRL 40,538

(1) 3,4-Methylenedioxybenzylthio-acetic acid

A solution of 18.24 g (0.24 mol) of thiourea in 104 ml of 48% strength hydrobromic acid and 20 ml of water is introduced into a one liter three-necked flask equipped with a magnetic stirrer and a condenser. The mixture is heated to 60° C. and 30.4 g (0.2 mol) of piperonyl alcohol are introduced. The temperature is raised to 95° C. and the mixture is allowed to cool. Crystals of thiouronium salt appear; these are filtered off and suction-drained. The precipitate thus obtained is introduced into a 500 ml three-necked flask together with 60 ml of sodium hydroxide solution. The mixture is heated to 70° C. and 15.6 g (0.164 mol) of chloroacetic acid in 30 ml of water are added dropwise. The whole is then heated under reflux for half an hour, after which it is cooled. The mixture is acidified with 3 N HCl, the precipitate obtained is redissolved in a dilute (sodium) bicarbonate solution, and the solution is washed with methylene chloride, filtered over charcoal and again acidified with 3 N HCl so as to precipitate 3,4-methylenedioxybenzylthio-acetic acid, which is filtered off. After recrystallisation fro a 1:1 (volume/volume) mixture of diisopropyl ether and petroleum ether, 18.2 g (40% yield) of the said acid (instantaneous melting point=87° C.) are collected.

(2) Ethyl 3,4-methylenedioxybenzylthio-acetate 18.08 g (0.08 mol) of the preceding acid are dissolved in 160 ml of 1,2-dichloroethane, and 16 ml of anhydrous ethanol and 1.6 ml of concentrated $H_2SO_4$ are added. The whole is heated under reflux for about 6 hours and is cooled, and the organic phase is decanted, the water formed being removed, and is washed with a dilute bicarbonate solution and then with water. The solution is then dried over $Na_2SO_4$ and the solvent is evaporated.

21 g of an orange-coloured oil are obtained; this is ethyl 3,4-methylenedioxybenzylthio-acetate (yield: 96%).

(3) 3,4-Methylenedioxybenzylthio-acetohydroxamic acid

The preceding product (0.085 mol) is added to a hydroxylamine solution prepared from 8.76 g (0.126 mol) of hydroxylamine hydrochloride in 210 ml of methanol and 4.83 g (0.21 gram atom) of sodium in 210 ml of anhydrous methanol. The whole is left in contact overnight at ambient temperature, the methanol is evaporated, the residue is taken up in water, the solution is filtered over charcoal and acidified with 3 N HCl and the precipitate thus obtained is filtered off and washed with water. 14.5 g (yield=70%) of 3,4-methylenedioxybenzylthio-acetohydroxamic acid are obtained. Instantaneous melting point=127°–128° C.; (yield: 70%).

(4) CRL 40,538

13.1 g (0.054 mol) of the preceding acid are introduced into a flask and 60 ml of acetic acid and 6.5 ml of $H_2O_2$ (~110 volumes strength) are added. The mixture is left in contact for about 3 hours at ambient temperature; white crystals appear. These are filtered off and washed with diisopropyl ether. After recrystallisation from a 1:1 (volume/volume) mixture of water and ethanol, 11 g of 3,4-methylenedioxybenzyl-sulphinyl-acetohydroxamic acid are obtained. Melting point=206° C. Yield: 79%.

EXAMPLE 33

3,4-Dimethoxybenzylsulphinyl-acetohydroxamic acid

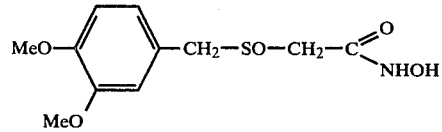

Code No. CRL 40,564

(1) 3,4-Dimethoxybenzylthio-acetic acid 13.07 g (0.172 mol) of thiourea and 86 ml of water are introduced into a 1 liter 3-necked flask equipped with a magnetic stirrer and a condenser. The mixture is heated to 50°–60° C. and 32 g (0.172 mol) of 3,4-dimethoxybenzylchloride are added in a single operation. The reactants are heated to reflux and boiling is maintained for 15 mins; the solution becomes limpid. Thereafter the mixture is cooled and a solution of 27.52 g (0.688 mol) of NaOH in 43 ml of water is introduced dropwise at about 60° C. Heating under reflux is again carried out for 30 minutes, the mixture is cooled and a solution of sodium chloroacetate (obtained by neutralising 22.76 g of chloroacetic acid in 172 ml of water with 20.23 g of NaHCO₃) is added dropwise at 60°–70° C. The whole is then heated under reflux for 30 minutes, cooled, filtered and then acidified with 3 N HCl. After recrystallisation from toluene, 28.7 g of 3,4-dimethoxybenzylthio-acetic acid are obtained. Yield: 69%. Instantaneous melting point: 94° C.

(2) Methyl 3,4-dimethoxybenzylthio-acetate 24.2 g (0.1 mol) of the above acid are dissolved in 200 ml of anhydrous methanol and 4 ml of concentrated sulphuric acid are added. The whole is heated under reflux for about 3 hours, the methanol is evaporated, the oil obtained is taken up in ether, the organic phase is washed with a dilute sodium bicarbonate solution and then with water, dried over $Na_2SO_4$ and the solvent is evaporated off. 24.2 g (yield: 94%) of the stated product, which is in the form of an orange-coloured oil, are thus collected.

(3) 3,4-Dimethoxybenzylthio-acetohydroxamic acid

The above product (0.0945 mol) is added to a solution of hydroxylamine, prepared from 9.95 g (0.143 mol) of hydroxylamine hydrochloride in 200 ml of methanol and 5.45 g (0.237 gram atom) of sodium in 200 ml of anhydrous methanol. The whole is left in contact overnight at ambient temperature, the mixture is filtered, the methanol is evaporated, the residue is taken up in water, the solution is filtered over charcoal and acidified with 3 N HCl, and the oil obtained is taken up in methylene chloride, the solution is dried over $Na_2SO_4$, the solvent is evaporated and the residue is taken up in ethyl acetate. After filtering off and washing with ether, 16.9 g (yield: 70%) of the stated product are obtained. Instantaneous melting point: 78° C.

(4) CRL 40,564

15.42 g (0.06 mol) of the above product are introduced into a flask and 60 ml of acetic acid and 7 ml of 110 volumes strength are added. The mixture is left in contact for about 2 hours at 20° C.; white crystals gradually appear and these are filtered off and dried. After recrystallisation from dimethylformamide, 11 g of CRL 40,564 are collected. Yield: 66%. Instantaneous melting point: 202° C.

EXAMPLE 34

5-(p-chlorophenyl)-ureido-acetohydroxamic acid

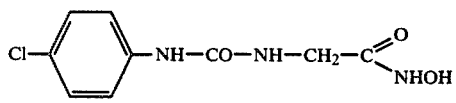

Code No. CRL 40,517

On proceeding as indicated in Example 26, but replacing the phenylisocyanate by p-chlorophenylisocyanate, the following products are successively obtained:

(1) ethyl 5-(p-chlorophenyl)-ureido-acetate (yield: 62%; melting point: 160°-161° C. ) and (2) CRL 40,517 by recrystallisation from a 1:1 (volume/volume) mixture of dimethylformamide and ethanol. Yield: 58%; melting point: 220°-222° C. (with decomposition).

EXAMPLE 35

α-Naphthylcarbamoylacetohydroxamic acid

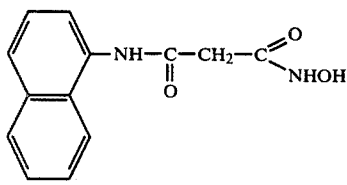

Code No. CRL 40,518

(1) Ethyl α-naphthylcarbamoyl acetate

A solution of 28.6 g (0.2 mol) of α-naphthylamine in 200 ml of anhydrous benzene is heated under reflux, whilst stirring, and a solution of 15 g (0.1 mol) of ethylmalonyl chloride in 50 ml of anhydrous benzene is added dropwise. The mixture is heated under reflux for a further hour and, the precipitate of α-naphthylamine hydrochloride is filtered off and washed with ether; the filtrate is washed with dilute HCl and with water, and is then dried and evaporated to dryness in vacuo, the residue is taken up in diisopropyl ether and the product is filtered off and recrystallised from a 1:1 (volume/volume) mixture of ethyl acetate and petroleum ether. 23.5 g (yield 91%) of the stated product are obtained. Melting point: 80°-81° C.

(2) CRL 40,518

19.3 g (0.075 mol) of ethyl α-naphthylcarbamoylacetate are treated with a solution of hydroxylamine, prepared from 5.6 g (0.08 mol) of hydroxylamine hydrochloride and 3.68 g of sodium in 250 ml of methanol. After leaving the reactants in contact for 5 hours, the mixture is evaporated to dryness in vacuo, the residue is taken up in 400 ml of cold water, the solution is filtered over charcoal, and the product is precipitated cold with 3 N HCl, filtered off and washed with water. CRL 40,518 is obtained by recrystallisation from ethanol. Yield: 62% Melting point: 184°-186° C. (with decomposition)

EXAMPLE 36

1-(4-Benzhydrylpiperazino)-acetohydroxamic acid hydrochloride

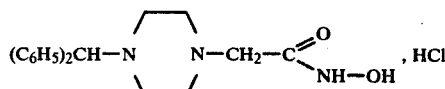

Code No. CRL 40,536

(1) Ethyl 1-(4-benzhydrylpiperazino)-acetate

A mixture of 17.5 g (0.07 mol) of benzhydrylpiperazine, 12.76 g (0.075 mol) of ethyl bromoacetate, 9.8 g (0.07 mol) of potassium carbonate and 0.1 g of potassium iodide in 180 ml of ethanol is heated for 4 hours under reflux, whilst stirring. After standing overnight, the mixture is evaporated to dryness in vacuo, the residue is taken up in 250 ml of ether, the solution is washed 3 times with water and is extracted with 3 N HCl, the extract is precipitated with $Na_2CO_3$ and the product is filtered off, washed with water and dried. 21.5 g (yield: 91%) of the stated product, melting at 54°-56° C., are obtained.

(2) CRL 40,536

A solution of hydroxylamine is prepared from 4.2 g (0.06 mol) of hydroxylamine hydrochloride and 2.5 g (0.11 gram atom) of sodium in 250 ml of methanol and is filtered, and 16.9 g (0.05 mol) of the preceding product are added to the filtrate. After leaving the reactants in contact overnight, the mixture is evaporated to dryness in vacuo, the residue is taken up in water, the solution is neutralised with 3 N HCl and extracted with methylene chloride, and the extract is washed with water and dried. It is evaporated in vacuo, the residue is taken up in a solution of hydrogen chloride in ethanol and the product is filtered off and recrystallised from ethanol, to give CRL 40,536. Melting point=206°-208° C. (with decomposition). Yield: 42%.

EXAMPLE 37

N,N-Diphenylureidoacetohydroxamic acid

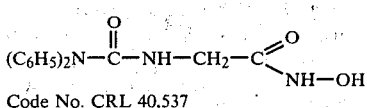

Code No. CRL 40,537

(1) Ethyl N,N-diphenylureidoacetate

A solution of sodium methylate is prepared from 4.6 g (0.2 gram atom) of sodium in 100 ml of anhydrous methanol and is run cold into a solution of 28 g (0.2 mol) of ethyl aminoacetate hydrochloride in 150 ml of methanol. The sodium chloride formed is filtered off, the filtrate is evaporated to dryness in vacuo and the residue is taken up in 200 ml of benzene; this solution is dried over sodium sulphate, filtered and evaporated. The oily residue is taken up in 100 ml of benzene and a solution of 21 g (0.09 mol) of diphenylcarbamoyl chloride in 50 ml of benzene is added dropwise at 25°–30° C. The mixture is stirred for a further 4 hours at 30° C. and is washed with water, dried and evaporated to dryness in vacuo, and the residue is recrystallised from ethanol; 20.8 g (yield: 78%) of the stated product, melting at 106° C., are obtained.

(2) CRL 40,537

18 g (0.06 mol) of the preceding product are added to 250 ml of a solution of hydroxylamine in methanol, obtained from 5.6 g (0.08 mol) of hydroxylamine hydrochloride and 3.45 g of sodium. After leaving the reactants in contact for 24 hours, the mixture is evaporated in vacuo, the residue is taken up in water, the solution is precipitated with 3 N HCl and the product is filtered off, washed with water, dried and recrystallised from dimethylformamide to give CRL 40,537. Melting point=228°–230° C. (with decomposition). Yield: 65%.

EXAMPLE 38

1-Adamantyl-carbamoyl-acetohydroxamic acid

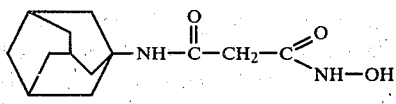

Code No. CRL 40,499

(1) Ethyl 1-adamantyl-carbamoyl-acetate 30.4 g (0.2 mol) of 1-adamantanamine are stirred in 200 ml of anhydrous benzene at 20° C. until dissolved, and a solution of 15 g (0.1 mol) of ethylmalonyl chloride in 30 ml of benzene is then run in over the course of 1 hour. After standing overnight, the adamantanamine hydrochloride is filtered off and washed with benzene, the filtrate is evaporated to dryness in vacuo and the residue is taken up in diisopropyl ether and filtered off. The desired product is obtained in a yield of 70%; it melts at 97°–98° C.

(2) CRL 40,499

15.1 g (0.057 mol) of the preceding product are added to a solution of hydroxylamine in methanol, prepared from 4.2 g (0.06 mol) of hydroxylamine hydrochloride and 2.75 g of sodium in 150 ml of anhydrous methanol. The mixture is stirred for 4 hours at 25° C., the methanol is evaporated in vacuo, the residue is taken up in 300 ml of water, the solution is acidified with 3 N HCl and the product is filtered off, washed with water, dried and recrystallised from ethanol to give CRL 40,499. Melting point=215°–216° C. (with decomposition). Yield: 57%.

The following text summarises a part of the results of the tests which were carried out with the products according to the invention, these products (unless otherwise stated) being administered intraperitoneally, in suspension in a gum solution (gum arabic), in a volume of 20 ml/kg in the case of mice and of 5 ml/kg in the case of rats.

Tests on CRL 40,373 (product of Example 1)

A. Toxicity:

No mortality whatsoever of isolated mice is observed at doses of 64 mg/kg, 128 mg/kg, 256 mg/kg, 512 mg/kg and 1,024 mg/kg.

B. Effect on the central nervous system:

(1) Interaction with apomorphine

Batches of six rats are each given a subcutaneous injection of apomorphine (0.5 mg/kg) 30 minutes after the administration of CRL 40,373. It is found that the stereotype behaviour induced in rats by apomorphine is not influenced by CRL 40,373.

(2) Interaction with amphetamine 30 minutes after the administration of CRL 40,373, amphetamine is injected intraperitoneally at a dose of 2 mg/kg. It is observed that CRL 40,373 inhibits the amphetamine-induced stereotypes, this inhibition being proportional to the doses.

(3) Interaction with reserpine

After intraperitoneal administration of reserpine (2.5 mg/kg), batches of 6 mice are each given CRL 40,373. It is observed that the hypothermia and ptosis induced by reserpine are not modified.

(4) Interaction with oxotremorine 30 minutes after the administration of CRL 40,373, batches of 12 mice are each given an intraperitoneal injection of oxotremorine (0.5 mg/kg). The following is observed:

As regards the temperature, CRL at doses of 128 mg/kg and 512 mg/kg exerts a hypothermia-inducing effect and aggravates the lowering of the temperature produced by oxotremorine, as regards trembling, CRL 40,373 has no significant influence on the trembling caused by oxotremorine, and as regards peripheral cholinergic symptoms, CRL 40,373 at high doses (128 and 512 mg/kg) increases the hypersalivation and hyperlacrymation produced by oxotremorine.

(5) Effect on the four-plate test, traction and electrical shock

The test is carried out on batches of 10 sensitive mice (EVIC CEBA strain), 30 minutes after the administration of CRL 40,373. It is observed that this product does not cause an increase in the number of incorrect moves, does not bring about any major motor incoordination and does not modify the convulsing effects of the electric shock.

(6) Effect on the motility (a) Spontaneous motility

Thirty minutes after having been given CRL 40,373, the mice (6 per dose, 12 comparison animals) are placed in an actimeter, where their motility is recorded for half an hour. It is observed that at large doses (128 and 512 mg/kg) CRL 40,373 causes a reduction in the (spontaneous) motor activity of the mice.

(b) Motility reduced by habituation to a cage (residual motility)

Mice which have remained for 18 hours in the actimeters are given CRL 40,373. They are immediately replaced in their cages and, after a period of half an hour, their motility is recorded for 30 minutes (6 animals per dose, 12 comparison animals). It is observed that CRL 40,373 does not cause a resumption of the exploring activity of mice accustomed to their environment.

(c) Motility reduced by hypoxia treatment

Thirty minutes after administration of CRL 40,373, the mice (10 per dose, 20 comparison animals) are subjected to anoxia by pressure reduction (depression of 600 mm Hg in 90 seconds, return to normal pressure in 45 seconds) and are then placed in an actimeter where their motility is noted for 10 minutes. It is observed that CRL 40,373 does not produce an improvement in the motor recovery of mice, of which the motility has been reduced by anoxia caused by lowering the pressure.

(7) Effect on inter-group aggressiveness

After three weeks' residence in each of the halves of a cage divided by an opaque partition, the mice receive CRL 40,373 thirty minutes before being brought together by withdrawing the partition. The number of fights which take place in the course of 15 minutes is noted, and it is observed that CRL 40,373 in a large dose reduces the number of fights.

It follows from these tests that CRL 40,373 is a sedative agent.

Tests on CRL 40,385 (product of Example 3)

A. Toxicity:

At the doses mentioned above, no mortality whatsoever is observed. It is found in isolated mice that, at large doses (1,024 mg/kg and 512 mg/kg), there is, on the one hand, sedation coupled with an increase in the fear reaction and, on the other hand, that pilo-erection occurs for 24 hours.

At doses of 32 mg/kg to 256 mg/kg it is found that the mice become excited and hyperreactive.

The $LD_{50}$ for intraperitoneal administration are as follows:

$LD_{50}$ (isolated mice): 1,500 mg/kg
$LD_{50}$ (mice in groups): 1,050 mg/kg.

It is found that CRL 40,385 is significantly more toxic to mice in groups than for isolated mice, the ratio $LD_{50}$ (isolated mice)/$LD_{50}$ (mice in groups) being 1.43. Although there is a higher toxicity for mice in groups, this cannot be called group toxicity.

B. Effect on the central nervous system:

(1) Interaction with apomorphine

Batches of 6 rats are given a subcutaneous injection of 0.5 mg/kg of apomorphine 30 minutes after the administration of CRL 40,385. It is observed that, at a large dose, CRL 40,385 causes an increase in the duration of the stereotypies induced by apomorphine.

(2) Interaction with amphetamine

Thirty minutes after the administration of CRL 40,385 the rats are given an intraperitoneal injection of 2 mg/kg of amphetamine (6 animals per dose). It is observed that. at a dose of 256 mg/kg, CRL 40,385 causes a lengthening of the duration of the amphetamine-induced stereotypies.

(3) Interaction with reserpine

Four hours after the administration of reserpine (2.5 mg/kg intraperitoneally) the mice are given CRL 40,385. The following is observed:

at doses of 64, 128 and 256 mg/kg, CRL 40,385 exerts a moderate antagonism towards reserpine-induced hypothermia and CRL 40,385 does not modify the intensity of the palpebral ptosis induced by reserpine.

(4) Interaction with oxotremorine

Thirty minutes after the administration of CRL 40,385, the mice (6 per dose) are given an intraperitoneal injection of 0.5 mg/kg of oxotremorine. The following is observed:

(a) as regards the temperature, CRL 40,385 at doses of 32 and 128 mg/kg exerts a very partial antagonism against the hypothermia produced by oxotremorine.

(b) as regards trembling, CRL 40,385 causes, at 128 mg/kg. and above all at 512 mg/kg, a reduction in the intensity of the trembling movements produced by oxotremorine and (c) as regards peripheral cholinergic symptoms, CRL 40,385 does not modify the increase in salivation, lachrymation and defaecation, occurring after an injection of oxotremorine.

(5) Effect on the four-plate test, traction and electrical shock

Batches of 10 mice are subjected to the test thirty minutes after having received CRL 40,385. It is observed that CRL 40,385 does not produce an increase in the number of incorrect moves, does not cause a major motor deficiency and, in a large dose, counteracts the convulsing effects of the electrical shock.

(6) Effect on the motility (a) Spontaneous motility

Thirty minutes after having been given CRL 40,385, the mice are placed in actimeters where their motility is recorded for half an hour. It is found that, at doses of 128 and 256 mg/kg, CRL 40,385 causes a moderate increase in the spontaneous motor activity. This effect disappears at a larger dose.

(b) Motility reduced by habituation to the cage

After remaining for 18 hours in the actimeters, the mice receive CRL 40,385. Immediately afterwards they are replaced in their cage and half an hour afterwards the recording of the motility starts and is continued for 30 minutes. It is observed that, from a dose of 32 mg/kg upwards, CRL 40,385 causes a resumption of activity in animals habituated to their cage.

(c) Motility reduced by hypoxia treatment

Half an hour after administration of CRL 40,385, the mice (10 per dose, 20 comparison animals) are subjected to anoxia by pressure reduction (depression of 600 mm Hg in 90 seconds, return to normal pressure in 45 seconds) and are then placed in the actimeters, where their motility is noted for the following 10 minutes. It is observed that CRL 40,385 causes an improvement in the motor recovery of mice, of which the motility has been reduced by exposure to hypoxia. This effect appears at a dose of 32 mg/kg and increases with the dose up to 512 mg/kg administered intraperitoneally.

(7) Effect on inter-group aggressiveness

After 18 days' residence on either side of a partition separating their cage in the middle, groups of 3 mice receive CRL 40,385 and are brought together half an hour later by withdrawing the partition, and the number of fights which take place in the course of 15 minutes is noted. It is found that CRL 40,385 reduces the aggressiveness.

(8) Investigations into an anticataleptic effect

CRL 40,385 or amantadine are administered intraperitoneally 4 hours and 30 minutes after the injection of prochlorperazine (12.5 mg/kg administered intraperitoneally). The catalepsy is assessed every 30 minutes by the plug test (9 cm), the four plug test, the test using parallel bars and the test of crossing the paws on the same side. It is observed that CRL 40,385, at a dose of 256 mg/kg, counteracts the cateleptigenic action of prochlorperazine. However, this effect remains less intense than that of an 8 times smaller dose of amantadine.

(9) Effect on prolonged conditioning to take avoiding action

Rats placed in a shuttle box are conditioned to avoid an electric shock by changing sides. The shock is preceded by a sound and light stimulus lasting 3 seconds, which ceases when sides are changed or after 8 seconds. The sequence is repeated every 20 seconds. Animals conditioned for several tens of minutes show a percentage of avoidance which is close to 100%. They continue to be subjected to the stimulus every 30 seconds and gradually they reach a state in which they are no longer able to change sides during the period of 3 seconds during which no shock is delivered. After 24 hours, the animals appear to have lost their conditioning and virtually do not avoid any shock.

CRL 40,385 is then administered and the resumption of avoiding action, if it occurs, is followed until the effect disappears. It is observed that this product causes a resumption of avoiding actions in animals, the conditioning of which has disappeared after a prolongation of the treatment. As a first approximation, such an effect can be linked to a resumption of conditioned activity in a tired animal.

It follows from these tests that CRL 40,385 acts on the central nervous system. Some of its effects recall an anti-depressant type of activity, and others recall a psychostimulant type of activity. Nevertheless, the most marked property is the anti-fatigue activity, with the product acting not like an amphetamine substance (absence of a particular toxicity in groups of mice), but rather like a dopaminomimetic substance (like, for example, piribedile, methylergometrine, amantadine, apomorphine and dopa coupled with carbidopa, although CRL 40,385 does not have a hypothermic action like these).

C. Action on the cardio-vascular system

In the tests reported below, CRL 40,385 was administered in suspension in a solution of gum arabic, in a volume of 2 ml/kg. The hypotensive action was studied in awake rats with spontaneous hypertension. One batch of 7 rats is given 100 mg/kg of CRL 40,385 orally, followed, 2 hours later, by a fresh dose of 100 mg/kg of this product.

It is found, after the first administration, that:

the arterial pressure reduces by an average of 10% and the pulse rate reduces by 8% (a statistically significant result) by changing from 364 to 334 beats/minute.

It is found after the second administration that:

the arterial pressure falls progressively and reaches its minimum 4 hours after the second administration, the arterial pressure changing from 166 mm Hg to 142 mm Hg (representing a statistically significant reduction of 13%) and the pulse rate does not vary.

The psycho-stimulant properties of CRL 40,385 and its hypotensive effect at a dose of 100 mg/kg administered orally make it possible to envisage this compound being indicated in therapy as an anti-fatigue agent.

Tests on CRL 40,382 (product of Example 2)

CRL 40,382 has an original psychopharmacological profile characterised by an antagonism to the stereotypies induced by amphetamine, without altering the other effects of this substance (hypermotility, group toxicity). This antagonism appears specific to stereotypies induced by amphetamine because CRL 40,382 does not counteract the effect of apomorphine and of methylphenidate.

Furthermore, CRL 40,382 brings about a moderate hypomotility and, whilst it does not in itself cause catalepsy, it boosts the cataleptigenic effects of a preliminary dose of a neuroleptic agent.

The mechanism of action of CRL 40,382 appears different from that of all the substances which oppose stereotypies induced by amphetamine, it appears rather improbable that CRL 40,382 acts like α-methyltyrosine in inhibiting the synthesis of dopamine;

a blockage of the dopaminergic receptor comparable to that observed with the conventional neuroleptic agents (phenothiazines and butyrophenones) cannot be repressed (?) in the absence of antagonism to the effects of oxotremorine;

the depletion or the inactivation of a pool (?) of amines sensitive to amphetamine appears the most probable hypothesis.

In this respect, CRL 40,382 differs from reserpine as well as from tetrabenazine, which deplete other pools of dopamine.

Furthermore, the moderate sedative activity and the absence of catalepsy and of motor incapacity indicate that CRL 40,382 exerts an antipsychotic activity associated with a moderate sedative effect, without danger of bringing about secondary neurological effects.

Tests on CRL 40,400 (product of Example 4)

A. Toxicity:

At doses of 128 mg/kg, 256 mg/kg, 512 mg/kg and 1,024 mg/kg, CRL 40,400 does not cause any mortality whatsoever in isolated mice.

B. Effect on the central nervous system

CRL 40,400 does not modify the stereotypies induced in rats by apomorphine and amphetamine and in mice by oxotremorine and reserpine. On the other hand, it is observed that CRL 40,400 acts on the motility of mice.

Tests on CRL 40,411 (product of Example 5)

The maximum non-lethal dose (LD-O) in mice is greater than 1,024 mg/kg. In rats, CRL 40,411 inhibits the stereotypies induced by amphetamine, but does not modify those induced by apomorphine and methylphenidate. In mice, it moderately inhibits the hypothermia induced by reserpine without acting on the ptosis induced by reserpine. At doses equal to or greater than 64 mg/kg, it brings about a reduction in the motor activity in mice. The totality of the tests which have been carried out shows that CRL 40,411 exhibits a psychopharmacological profile similar to that of CRL 40,382 described above.

Tests on CRL 40,258 (product of Example 6)

A. Toxicity

Doses of 1,024 mg/kg and 512 mg/kg cause death in mice in 35 minutes and 24 hours, respectively. The LD-O is greater than 256 mg/kg.

B. Effect on the central nervous system (1) Interaction with reserpine

At a high dose, CRL 40,258, which is a hypothermia-inducing agent, aggravates the hypothermia induced by reserpine. At doses of 128 mg/kg and 32 mg/kg, it aggravates the ptosis induced by reserpine.

(2) Interaction with oxotremorine

In mice, CRL 40,258 contributes its effect to the hypothermia-inducing action of oxotremorine but does not alter the intensity or duration of the trembling movements induced by oxotremorine.

(3) Effect on the four-plate test, traction and electrical shock

At high doses (32 and 128 mg/kg) it is found that CRL 40,258 causes a substantial motor incapacity, and an increase in the lethal effects of the electric shock, in mice.

(4) Effect on the motility in mice

From a dose of 8 mg/kg upwards, it causes a reduction of the motor activity. On the other hand, the residual motility and the motor recovery after hypoxia are not improved.

Tests on CRL 40,438 (product of Example 7)

A. Toxicity

In mice, the LD-O is greater than 1,024 mg/kg.

B. Effect on the central nervous system

The psychopharmacological study of CRL 40,438 shows a certain number of effects of the excitation-inducing type:

hyper-reactivity in mice, the presence, at a high dose, of stereotype movements, and boosting of the stereotypies induced by apomorphine and by amphetamine, a moderate increase in the spontaneous motor activity, but a very marked stimulant effect where the motility has been reduced by habituation to the cage, and an effect of the "anti-fatigue" type on the prolonged avoidance test.

Furthermore, CRL 40,438 moderately opposes hypothermia and ptosis induced by reserpine, and the trembling movements caused by oxotremorine, and, at a high dose, reduces the aggressive behaviour of mice.

The effects observed after administration of CRL 40,438 come close to those described for CRL 40,385 and can suggest an activity of the anti-depressant type or of the psychostimulant type.

The working details, and the results, of the prolonged avoidance test referred to above are as follows:

Rats placed in a "shuttle box" are conditioned to avoid an electric shock lasting 5 seconds, by changing sides. The shock is preceded, for 3 seconds, by a sound and light stimulus which ceases when the rat changes side, or at the end of 8 seconds. The sequence repeats every 20 seconds. The animals which have been conditioned in some tens of minutes exhibit a percentage avoidance (change of side during the sound and light stimulus before the electric shock has been delivered) approaching 100%. They continue to be subjected to the stimulus every 20 seconds and gradually they no longer succeed in avoiding the shock. After 24 hours, the animals appear to have lost all conditioning and virtually do not avoid any shock.

CRL 40,438 is then administered and any resumption of the avoidance movements is followed until the effect ceases.

At doses of 64, 128 and 256 mg/kg administered intraperitoneally, CRL 40,438 causes a resumption of the avoidance behaviour in the animals whose conditioning has disappeared following a prolongation of the session.

Tests on CRL 40,439 (product of Example 8)

A. Toxicity

In mice, the LD-O is greater than 1,024 mg/kg. At a dose of 1,024 mg/kg, the animals exhibit a moderate excitation phase for 10 minutes followed by sedation with reduction of the reaction to the touch and of the muscular force. At doses of 512 mg/kg and 256 mg/kg, only sedation and reduction of the muscular force are observed. At a dose of 128 mg/kg, none of these symptoms is observed.

B. Effect on the central nervous system

CRL 40,439 increases, at a dose of 512 mg/kg, the hypothermia-inducing effect of reserpine and of oxotremorine. It does not affect reserpine-induced ptosis and moderately reduces the intensity of the trembling movements due to oxotremorine.

In mice, CRL 40,439, at a dose of 512 mg/kg, brings about a very great reduction in the spontaneous motility, and at a dose of 128 mg/kg causes a resumption of the motor activity in animals habituated to their cage and does not improve the motor recovery in animals whose motility has been reduced by anoxia induced by pressure reduction.

Finally, CRL 40,439 moderately reduces the inter-group aggressiveness in mice.

Tests on CRL 40,446 (product of Example 9)

A. Toxicity

At doses of 16, 32, 64, 128, 512 and 1,024 mg/kg, in mice, CRL 40,446 does not cause any mortality whatsoever.

B. Effect on the central nervous system

At a dose of 512 mg/kg, CRL 40,446 partially antagonises hypothermia induced by reserpine; on the other hand, ptosis induced by reserpine is not affected. CRL 40,446 reduces the spontaneous motility in mice at doses of 128 and 512 mg/kg and does not cause any resumption in the motor activity of mice (whether these are habituated to their cage or have been subjected to anoxia caused by pressure reduction). It reduces, to a moderate degree, inter-group aggressiveness in mice.

Tests on CRL 40,447 (product of Example 10)

A. Toxicity

In mice, the LD-O is greater than 1,024 mg/kg. At doses of 8 and 32 mg/kg (mice) and 64 mg/kg (rats), CRL 40,447 causes sedation for 30 to 60 minutes.

B. Effect on the central nervous system

At a dose of 512 mg/kg, CRL 40,447 reduces the spontaneous motility of mice.

Tests on CRL 40,450 (product of Example 11)

A. Toxicity

In mice, the LD-O is greater than 1,024 mg/kg.

B. Effect on the central nervous system

At a high dose (512 mg/kg), CRL 40,450 aggravates the hypothermia induced by reserpine and by oxotremorine and reduces the intensity of the trembling movements due to oxotremorine. Furthermore, it causes a reduction in the spontaneous motility of mice at a dose of 512 mg/kg. At doses of 512 and 256 mg/kg, it reduces the inter-group aggressiveness in mice.

Tests on CRL 40,464 (product of Example 12)

A. Toxicity

In mice, the LD-O is greater than 1,024 mg/kg.

B. Effect on the central nervous system

CRL 40,464, at a dose of 256 mg/kg, reduces the intensity of amphetamine-induced stereotypies. It aggravates the hypothermia due to oxotremorine and moderately reduces the intensity of the trembling movements caused by the latter. CRL 40,464 reduces the spontaneous motility in mice and at a dose of 128 mg/kg causes a resumption of the motor activity in animals habituated to their cage.

Tests on CRL 40,466 (product of Example 14)

A. Toxicity

In mice, at doses of 256 mg/kg, 512 mg/kg and 1,024 mg/kg, CRL 40,466 does not cause any mortality whatsoever; the animals exhibit sedation, with increase in the reactivity to the touch, increase in ptosis and increase in hypothermia.

B. Effect on the central nervous system

CRL 40,466 does not markedly alter the stereotypies induced in rats by apomorphine and amphetamine. It does not oppose hypothermia induced by oxotremorine; at high doses, it aggravates the hypothermia. It reduces the trembling movements due to oxotremorine.

At a high dose (512 mg/kg), CRL 40,466 depresses spontaneous motility in mice; at a low dose (8 mg/kg), it appears to exhibit a stimulant effect on the motility.

Psychopharmacological study of CRL 40,466 reveals effects of the sedative type and effects of the psychostimulant type. The effects of the sedative type are:

sedation in mice with, at a high dose, reduction in spontaneous motility, hypo-reactivity and motor incapacity, ptosis, hypothermia, reduction of aggressiveness at high doses, and antagonism to convulsions caused by electric shock.

The effects of the psychostimulant type are:

excitation, with hyper-reactivity, in rats and, at a low dose, in mice, moderate increase in the motility reduced by habituation or by the effects of hypoxia, and increase in aggressiveness, at a low dose.

Furthermore, CRL 40,466 produces a moderate (but significant) increase in the number of incorrect moves in the four-plate test, but this effect perhaps only reflects the excitation-inducing component of the product.

Tests on CRL 40,468 (product of Example 15)

A. Toxicity

At a dose of 1,024 mg/kg, CRL 40,468 causes the appearance of sedation with ptosis, reduction in the reactivity to the touch and depression of the respiration; the mice are found dead 24 hours after the injection. At a dose of 512 mg/kg, the symptoms are comparable, but no mortality is observed. At lower doses (256, 128, 64 and 32 mg/kg), the behaviour of the mice is comparable to that of the comparison animals.

B. Effect on the central nervous system

CRL 40,468 has an effect on the inter-group aggressiveness in mice. At a high dose, it reduces the number of fights.

Tests on CRL 40,471 (product of Example 16)

A. Toxicity

In mice, the LD-O is greater than 1,024 mg/kg. At the doses tested (1,024, 512, 256, 128 and 64 mg/kg) in mice, a reduction in the motility is observed.

B. Effect on the central nervous system

In rats, CRL 40,471 does not alter the stereotypies induced by amphetamine and by apomorphine. In mice, it exerts a moderate antagonism against reserpine-induced hypothermia.

At a high dose (512 mg/kg), CRL 40,471 very greatly reduces the spontaneous motility of mice. CRL 40,471 does not cause a resumption of the motor activity in mice habituated to their cage. Finally, CRL 40,471 does not improve the motor recovery in mice whose motility has been depressed following anoxia induced by pressure reduction. However, it should be noted that the mice which have received a high dose of CRL 40,471 (512 mg/kg) exhibit a motor recovery comparable to that of the comparison mice whilst this dose produces a very great reduction in the spontaneous motor activity.

At high doses, CRL 40,471 reduces the intra-specific aggressiveness in mice.

In conclusion, CRL 40,471 exhibits a sedative activity. It should however be noted, firstly, that an effect of the anti-aggressive type appears to manifest itself in the absence of any hypomotility, and, secondly, that the motility-depressing effect observed at a high dose is not found when the motor activity has been depressed by hypoxia induced by pressure reduction.

Tests on CRL 40,475 (product of Example 19)

A. Toxicity

In mice, the LD-O is greater than 1,025 mg/kg.

B. Effect on the central nervous system

At doses of 32, 128 and 256 mg/kg, CRL 40,475 reduces the intensity of amphetamine-induced stereotypies in rats. It does not influence the stereotypies induced by apomorphine. In mice, it partially opposes the hypothermia-inducing action of oxotremorine.

At high doses (128 mg/kg and above), CRL 40,475 produces a large reduction in the spontaneous motor activity of mice, whilst at the lowest dose used (8 mg/kg) a slight hypermotility is observed.

At doses of 2, 8 and 32 mg/kg, CRL 40,475 causes a moderate resumption of activity in mice habituated to their cage.

CRL 40,475 does not produce an improvement in the motor recovery in mice whose motility has been reduced by anoxia induced by pressure reduction. However, it should be noted that the dose of 128 mg/kg, which caused a reduction in the spontaneous motor activity, does not alter the activity of mice who have undergone anoxia induced by pressure reduction.

In conclusion, the psychopharmacological study of CRL 40,475 shows that this product is a sedative and anti-convulsive agent.

Tests on CRL 40,490 (product of Example 20)

A. Toxicity

In mice, the LD-O is greater than 1,024 mg/kg.

B. Effect on the central nervous system

CRL 40,490 at a dose of 128 mg/kg combats hypothermia induced by reserpine. At a dose of 512 mg/kg, it reduces the motor activity of mice.

Tests on CRL 40,491 (product of Example 21)

A. Toxicity

In mice, the LD-O is greater than 1,024 mg/kg (no mortality 24 hours after administration).

B. Effect on the central nervous system

At a dose of 256 mg/kg, CRL 40,491 reduces the intensity of amphetamine-induced stereotypies. At a dose of 512 mg/kg, it produces a reduction in the spontaneous motility of mice. At a dose of 256 mg/kg, it reduces the inter-group aggressiveness of mice and causes a moderate resumption of the activity of mice habituated to their cage.

Tests on CRL 40,500 (product of Example 22)

A. Toxicity

CRL 40,500 is more toxic than the products studied above. At doses of 1,024 and 512 mg/kg, it causes the rapid appearance of sedation with reduction of the muscular force and muscle tonus, and the rapid appearance of hypothermia: the animals exhibit a lurching gait and death occurs, on average, after 2 hours 30 minutes and 18 hours, respectively. At a dose of 256 mg/kg, the symptoms are identical but the mice survive. At lower doses (128, 64 and 32 mg/kg), only the sedation still appears.

B. Effect on the central nervous system

CRL 40,500 does not alter the stereotypies induced by apomorphine (rats and mice) and by amphetamine (rats). It causes an aggravation of the hypothermia due to reserpine and to oxotremorine. It increases the peripheral effects of oxotremorine at doses of 128 and 32 mg/kg.

At doses of 32 and 128 mg/kg, CRL 40,500 moderately reduces the spontaneous motility of mice. At a dose of 128 mg/kg it causes a moderate resumption of the motor activity of mice habituated to their cage. It does not cause a marked improvement in the motor recovery of mice depressed by anoxia caused by pressure reduction.

At all the doses studied, CRL 40,500 reduces the inter-group aggressiveness of mice. However, this effect, which is present with considerable intensity from the lowest dose used (8 mg/kg), does not increase with the doses; rather, a reduction of the effect is observed at high doses (64 and 128 mg/kg).

Summarising, the psychopharmacological profile of CRL 40,500 includes the presence of moderate sedation at high doses and a reduction of aggressiveness which is substantial at low doses.

Tests on CRL 40,509 (product of Example 23)

A. Toxicity

In mice, the LD-O is greater than 512 mg/kg but less than 1,024 mg/kg.

B. Effect on the central nervous system

From a psychopharmacological point of view, CRL 40,509 is characterised by the presence of:
sedation at a high dose (256 mg/kg),
an effect of the anti-anoxia type at lower doses (64 and 128 mg/kg), and
an effect of the anti-aggressive type at very low doses (8 and 16 mg/kg).

Tests on CRL 40,510 (product of Example 25)

CRL 40,510, in suspension in a solution of gum arabic, or in solution in distilled water (solubility limit #1.3%) was administered intraperitoneally in a volume of 20 ml/kg in the case of mice and 5 ml/kg in the case of rats.

A. Toxicity

In mice, the LD-O is greater than 1,024 mg/kg.

B. Effect on the central nervous system

The psychopharmacological study of CRL 40,510 has shown that this product exhibits effects of the anxiolytic type (four plate test) and of the anti-convulsive type (these effects, observed after intraperitoneal administration, also manifest themselves after gastric administration). Furthermore, CRL 40,510 exerts a moderate sedative effect at high doses.

CRL 40,510 thus comes close to the benzodiazepines in respect of anxiolytic and anti-convulsive activities, but differs in respect of the absence of motor incapacity and in respect of relative resistance to sedation.

Furthermore, like the benzodiazepines, CRL 40,510 is moderately antagonistic to the trembling movements caused by oxotremorine.

Tests on CRL 40,513 (product of Example 26)

A. Toxicity

In mice, the LD-O is greater than 1,024 mg/kg. At high doses, sedation and hypothermia are observed.

B. Effect on the central nervous system

The psychopharmacological study of CRL 40,513 shows an anti-aggressive effect and an improvement in the motor recovery of mice whose motility has been reduced by anoxia induced by pressure reduction.

Tests on CRL 40,498 (product of Example 28)

A. Toxicity

In mice, the LD-O is greater than 1,024 mg/kg. At doses of 256 mg/kg and above, sedation, depressed respiration and reaction to the touch are observed.

B. Effect on the central nervous system

The psychopharmacological study of CRL 40,498 shows
sedation with reduction in motility, in aggressiveness and in reactivity, and hypothermia, at a high dose, without motor incapacity,
an increase in the number of incorrect moves in the four plate test at a range of doses from 512 to 2 mg/kg administered intraperitoneally, and from 512 to 32 mg/kg (and possibly less) administered gastrically,
partial antagonism to reserpine-induced hypothermia without alteration of the ptosis and without alteration of the other hypothermia studied (induced by oxotremorine or by apomorphine), and
a discrete stimulant effect on the motility in mice whose motor activity has been depressed by anoxia induced by pressure reduction.

In general terms, the pharmacological and clinical tests taken together show that the products according to the invention are substances which act on the central nervous system as psychotropic agents and more precisely as sedatives, anti-depressants, psychostimulants or anxiolytics, the sedative activity being common to all the products.

The particularly interesting products according to the invention are the products of Examples 1 (CRL 40,373), 2 (CRL 40,382), 3 (CRL 40,385, which is the preferred product), 14 (CRL 40,466), 16 (CRL 40,471), 20 (CRL 40,490), 21 (CRL 40,491), 23 (CRL 40,509), 25 (CRL 40,510), 26 (CRL 40,513) and 28 (CRL 40,498).

The product of Example 1 (CRL 40,373) has been used clinically with success as a sedative, in the form of a tablet containing 100 mg of active principle, at the rate of 1 to 3 tablets per day.

The product of Example 2 (CRL 40,382) has been used clinically with success as a sedative, in the form of a tablet containing 250 mg of active principle, at the rate of 2 to 3 tablets per day.

The product of Example 3 (CRL 40,385) has been used clinically with success for anti-fatigue treatment, in the form of a tablet or pill (in each case containing 100 mg of active ingredient), at the rate of 2 to 3 tablets or pills per day.

The product of Example 16 (CRL 40,471) has given good results clinically as a sedative in the form of a tablet containing 0.250 mg of active ingredient, at the rate of 2 tablets per day.

The product of Example 25 (CRL 40,510) has been used with good results in man as an anxiolytic sedative agent, in the form of a pill containing 20 mg of active ingredient, at the rate of 3 to 4 pills per day.

The product of Example 28 (CRL 40,498) has given good results clinically as an anxiolytic agent in the form of a pill containing 100 mg of active ingredient, at the rate of 2 pills per day.

We claim:

1. A compound selected from acetohydroxamine acid, a non-toxic metal salt of said acid or a non-toxic acid addition salt of said acid, said acid being of the formula:

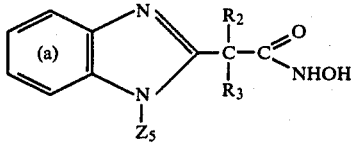

in which $R_2$ and $R_3$ are individually selected from hydrogen or $C_1$ to $C_6$ alkyl and $Z_5$ is phenyl or naphthyl, or phenyl or naphthyl substituted with one or two substituents selected from $C_1$ to $C_4$ alkyl, $C_1$ to $C_4$ alkoxy, methylenedioxy, halogen, $CF_3$, $NO_2$ or $NH_2$ and the nucleus (a) being unsubstituted or substituted with one or two substituents selected from $C_1$ to $C_4$ alkyl, $C_1$ to $C_4$ alkoxy, methylenedioxy, halogen, $CF_3$, $NO_2$ or $NH_2$.

2. A compound according to claim 1, in which $R_2$ is H, $CH_3$ or $C_2H_5$, $R_3$ is H, and $Z_5$ is phenyl or halogenophenyl.

3. 2-(1-Phenylbenzimidazolyl)-acetohydroxamic acid and its non-toxic metal salts.

4. A composition comprising a psychotropically effective amount of a compound of claim 1 in association with a pharmaceutically acceptable excipient.

* * * * *